(12) United States Patent
Hosaka et al.

(10) Patent No.: US 8,648,001 B2
(45) Date of Patent: Feb. 11, 2014

(54) AMINOSILANE COMPOUNDS, CATALYST COMPONENTS AND CATALYSTS FOR OLEFIN POLYMERIZATION, AND PROCESS FOR PRODUCTION OF OLEFIN POLYMERS WITH THE SAME

(75) Inventors: Motoki Hosaka, Chigasaki (JP); Takefumi Yano, Chigasaki (JP); Maki Sato, Chigasaki (JP); Kohei Kimura, Chigasaki (JP)

(73) Assignee: Toho Titanium Co., Ltd., Chigasaki-Shi (JP)

( * ) Notice: Subject to any disclaimer, the term of this patent is extended or adjusted under 35 U.S.C. 154(b) by 6 days.

(21) Appl. No.: 13/289,728

(22) Filed: Nov. 4, 2011

(65) Prior Publication Data
US 2012/0053310 A1    Mar. 1, 2012

Related U.S. Application Data

(62) Division of application No. 11/916,039, filed as application No. PCT/JP2006/311038 on May 26, 2006, now abandoned.

(30) Foreign Application Priority Data

May 31, 2005 (JP) ................................ 2005 158823
May 31, 2005 (JP) ................................ 2005 158826

(51) Int. Cl.
| | |
|---|---|
| B01J 31/00 | (2006.01) |
| B01J 21/00 | (2006.01) |
| C08F 4/44 | (2006.01) |
| C08F 4/42 | (2006.01) |
| C08F 4/06 | (2006.01) |
| C08F 2/00 | (2006.01) |
| C08F 4/00 | (2006.01) |

(52) U.S. Cl.
USPC ........... 502/116; 502/123; 502/124; 502/158; 502/167; 502/232; 526/125.3; 526/126; 526/128; 526/141; 526/147; 526/217; 526/236

(58) Field of Classification Search
USPC .............. 526/126, 128, 125.3, 141, 147, 217, 526/236; 502/123, 167
See application file for complete search history.

(56) References Cited

U.S. PATENT DOCUMENTS 3,431,222 A * 3/1969 Walter ........................... 528/14
3,911,169 A 10/1975 Lesaicherre et al.
(Continued)

FOREIGN PATENT DOCUMENTS

EP    0 578 470    1/1994
JP    57 63310    4/1982
(Continued)

OTHER PUBLICATIONS

Semenova E.A. et al., "Reaction of Dialkyldichloro and Alkyldichloro-Silanes with Methylamine," Bulletin of the Academy of Sciences of the USSR, Division of Chemical Sciences, Vol. 11, pp. 1945-1947, Nov. 1962, XP007913920.

(Continued)

Primary Examiner — David Buttner
Assistant Examiner — Elizabeth Eng
(74) Attorney, Agent, or Firm — Oblon, Spivak, McClelland, Maier & Neustadt, L.L.P.

(57) ABSTRACT

A catalyst for polymerization of olefins formed from (A) a solid catalyst component containing magnesium, titanium, halogen, and an electron donor compound, (B) an organoaluminum compound shown by the formula, $R^6_p AlQ_{3-p}$, and (C) an aminosilane compound shown by the formula, $R^3_n Si(NR^4R^5)_{4-n}$; and a process for producing a catalyst for polymerization of olefins in the presence of the catalyst are provided. A novel aminosilane compound, a catalyst component for polymerization of olefins having a high catalytic activity, capable of producing polymers with high stereoregularity in a high yield, and exhibiting an excellent hydrogen response, a catalyst, and a process for producing olefin polymers using the catalyst are provided.

7 Claims, 1 Drawing Sheet

(56) References Cited

U.S. PATENT DOCUMENTS

| | | | |
|---|---|---|---|
| 5,494,872 | A | 2/1996 | Hosaka et al. |
| 5,498,770 | A | 3/1996 | Hosaka et al. |
| 5,684,173 | A | 11/1997 | Hosaka et al. |
| 5,932,510 | A | 8/1999 | Hosaka et al. |
| 5,965,478 | A | 10/1999 | Goto et al. |
| 6,034,188 | A * | 3/2000 | Sano et al. ............ 526/124.6 |
| 6,156,690 | A | 12/2000 | Hosaka |
| 6,228,793 | B1 | 5/2001 | Hosaka et al. |
| 6,664,209 | B1 | 12/2003 | Hosaka |
| 6,670,497 | B2 | 12/2003 | Tashino et al. |
| 6,770,586 | B2 | 8/2004 | Tashino et al. |
| 6,855,656 | B2 | 2/2005 | Hosaka et al. |
| 7,005,399 | B2 | 2/2006 | Hosaka |
| 7,141,634 | B2 | 11/2006 | Hosaka et al. |
| 7,208,435 | B2 | 4/2007 | Hosaka et al. |
| 7,704,910 | B2 | 4/2010 | Hosaka et al. |
| 2005/0054773 | A1 | 3/2005 | Hosaka et al. |
| 2009/0253873 | A1 | 10/2009 | Hosaka et al. |
| 2009/0253874 | A1 | 10/2009 | Hosaka et al. |
| 2010/0190938 | A1 | 7/2010 | Yano et al. |
| 2012/0004378 | A1 | 1/2012 | Hosaka |

FOREIGN PATENT DOCUMENTS

| | | |
|---|---|---|
| JP | 57 63311 | 4/1982 |
| JP | 63 3010 | 1/1988 |
| JP | 1 315406 | 12/1989 |
| JP | 8 157533 | 6/1996 |
| JP | 2003-231711 | 8/2003 |
| WO | 2004 016662 | 2/2004 |

OTHER PUBLICATIONS

Herbst-Irmer R., et al., "1,3-Dimethyl-1-2, 4-Bis(di-tert-butylfluorsilyl-methylamino)-cyclodiosph(III)-azan und-dithiocyclodiphosph(V)azan. Synthese und kristallstrukture N," Phosphorus, Sulfur and Silicon and the RElated Elements, vol. 112, No. 1-4, May 1996, pp. 185-192, XP009136199.

Ferreira M.L. et al., "Effect of Co- and non-copolymerizable Lewis bases in propylene polymerization with EtInd2ZrC12/MAO," Macromolecular Chemistry and Physics, vol. 202, No. 6, Mar. 2001, pp. 830-839, XP002265698.

Rakebrandt, H.J., et al., "Diamino-Di-Tert-Butylsilanes- Building Blocks for Cyclic $(SIN)_2$, $(SINBN)_2$, $(SIN_2SN)$, and Spirocyclic $(SIN_2)_2SI$, $(SIN_2SN)_2S$ Compounds", Zeitschrift fuer Anorganische und Allgemeine Chemie, vol. 623, No. 8, pp. 1264 to 1268. 1997.

Belelli, P.G., et al., "An Experimental Study of Metallocene Heterogenization in Inorganic and Bio-polymeric Supports for Olefin Polymerization," Current Trends in Polymer Science, vol. 5, 2000, pp. 79-90 XP009136212.

Taiwanese Office Action issued Aug. 28, 2012 in Patent Application No. 095119143 with English Translation.

Office Action issued Jul. 23, 2012 in Korean Application No. 10-2007-7030831 (With English Translation).

* cited by examiner

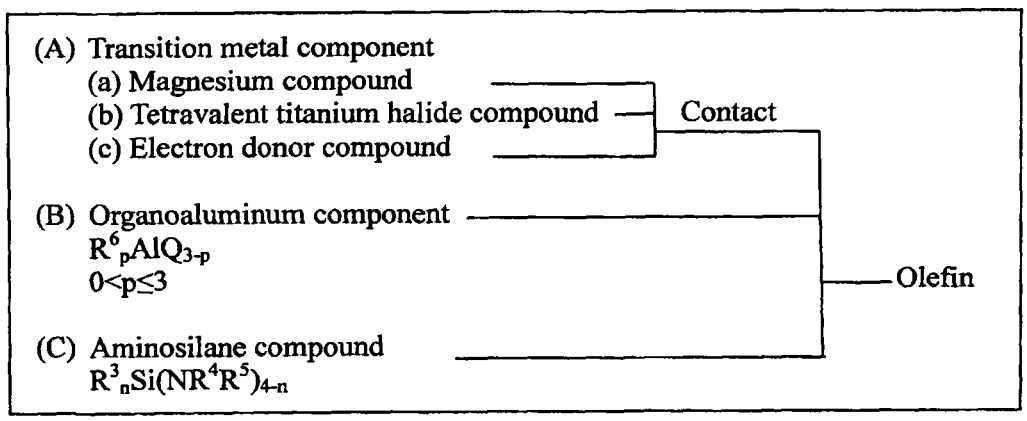

AMINOSILANE COMPOUNDS, CATALYST COMPONENTS AND CATALYSTS FOR OLEFIN POLYMERIZATION, AND PROCESS FOR PRODUCTION OF OLEFIN POLYMERS WITH THE SAME

CROSS REFERENCE TO RELATED APPLICATIONS

This application is a divisional application of U.S. application Ser. No. 11/916,039, filed on May 1, 2008, which is a 371 of PCT/JP06/311038, filed on May 26, 2006, and claims priority to the following applications: Japanese Patent Application No. 2005-158823, filed on May 31, 2005, and Japanese Patent Application No. 2005-158826, filed on May 31, 2005.

TECHNICAL FIELD

The present invention proposes a novel aminosilane compound, particularly a novel organosilicon compound which does not include an Si—OR bond which was indispensable as an olefin polymerization catalyst component used in general technologies, a catalyst component and a catalyst for polymerization of olefins in which the aminosilane compound is used, and a process for producing olefin polymers using the catalyst component and the catalyst.

BACKGROUND ART

A solid catalyst component containing magnesium, titanium, an electron donor compound, and a halogen as essential components used for polymerization of olefins such as propylene has been known in the art. A large number of methods for polymerizing or copolymerizing olefins in the presence of a catalyst for olefin polymerization comprising the above solid catalyst component, an organoaluminum compound, and an organosilicon compound have been proposed. For example, Patent Document 1 (JP-A-57-63310) and Patent Document 2 (JP-A-57-63311) propose a method for polymerizing olefins with three or more carbon atoms, in which a catalyst comprising a combination of a magnesium compound, a titanium compound, and an organosilicon compound having a Si—O—C bond is used. However, because these methods are not necessarily satisfactory for producing highly stereoregular polymers in a high yield, improvement of these methods has been desired.

Patent Document 3 (JP-A-63-3010) proposes a catalyst and a method for polymerizing propylene. The catalyst comprises a solid catalyst component, obtained by processing a powder produced from a dialkoxy magnesium, an aromatic dicarboxylic acid diester, an aromatic hydrocarbon, and a titanium halide with heat, an organoaluminum compound, and an organosilicon compound.

Patent Document 4 (JP-A-1-315406) proposes another catalyst for olefin polymerization and a method for polymerizing olefins in the presence of this catalyst. The catalyst for olefin polymerization comprises a solid catalyst component prepared by causing a suspension liquid containing diethoxymagnesium and an alkylbenzene to come in contact with titanium tetrachloride, reacting the suspension liquid with phthalic acid chloride, and causing the resulting solid product to come in contact with titanium tetrachloride in the presence of an alkylbenzene, an organoaluminum compound, and an organosilicon compound.

All of the above-described general technologies have attained certain results in improving catalytic activity to the extent of permitting dispensing with an ash-removal step for removing catalyst residues such as chlorine and titanium from formed polymers, improving the yield of stereoregular polymers, and improving durability of catalytic activity during polymerization. However, there is a demand for continued improvement of such a catalyst.

The polymers produced using these catalysts are used in a variety of applications including formed products such as vehicles and household electric appliances, containers, and films. These products are manufactured by melting polymer powders produced by polymerization, pelletizing the melted polymer, and forming the pellets into products using various molds. In manufacturing formed products, particularly, large products by injection molding or the like, melted polymers are sometimes required to have high fluidity (melt flow rate: MFR). In particular, for the purpose of cost reduction in the manufacturing of a highly functional block copolymer to be used as a vehicle material, in a method of producing a copolymer in an amount just required for obtaining an olefin-based thermoplastic elastomer (hereinafter referred to as "TPO") in a copolymerization reactor, and obtaining the TPO directly in the polymerization reactor without adding a separately-produced copolymer, that is, in so-called "manufacture of a reactor-made TPO by direct polymerization", a melt flow rate of 200 or more is demanded in a homopolymerization stage in order to produce a finished product with a high melt flow rate and to ensure easy injection molding. A number of studies to increase the melt flow rate while maintaining high stereoregularity of the polymer have been undertaken.

The melt flow rate greatly depends on the molecular weight of the polymers. In industry, hydrogen is generally added as a molecular weight regulator for polymers during polymerization of propylene. In this instance, a large quantity of hydrogen is usually added to produce low molecular weight polymers having a high melt flow rate. However, the quantity of hydrogen which can be added is limited because pressure resistance of the reactor is limited for the sake of safety.

In order to add a larger amount of hydrogen in vapor phase polymerization, the partial pressure of monomers to be polymerized has to be decreased, resulting in a decrease in productivity. The use of a large amount of hydrogen also brings about a problem of cost. As a method for solving this problem, Patent Document 5 (WO 2004-16662) proposes a method of producing a polymer having a high melt flow rate and high stereoregularity by using a compound shown by the formula $Si(OR^1)_3(NR^2R^3)$ as a catalyst component for polymerization of olefins.

However, because these methods are not necessarily satisfactory for basically solving the above problems of TPO production by direct polymerization, improvement of these methods has been desired.

(Patent Document 1) JP-A-57-63310 (Claims)
(Patent Document 2) JP-A-57-63311 (Claims)
(Patent Document 3) JP-A-63-3010 (Claims)
(Patent Document 4) JP-A-1-315406 (Claims)
(Patent Document 5) WO 2004-16662 (Claims)

Therefore, an object of the present invention is to provide an aminosilane compound, a catalyst component, and a catalyst for polymerization of olefins capable of excellently maintaining stereoregularity and yield of the polymer and capable of producing olefin polymers having a high melt flow rate with a given amount of hydrogen (excellent hydrogen response), and a method for producing an olefin polymer using the catalyst component or the catalyst.

DISCLOSURE OF THE INVENTION

In such circumstances, the inventors of the present invention have conducted extensive research. As a result, the inventors have discovered a novel alkylaminosilane compound which has a secondary amino group, but has no Si—OR bond and found that this compound has not been known as a useful catalyst component for olefin polymerization (although many organosilicon compounds having two or more Si—OR bonds have been known as industrial catalyst components for olefin polymerization, no such alkyl aminosilane compounds have been known), and that a catalyst formed from a solid catalyst component comprising magnesium, titanium, a halogen, and an electron donor compound, an organoaluminum compound, and the novel alkylaminosilane compound having a specific structure is more suitable than commonly known catalysts as a catalyst for olefin polymerization. These findings have led to the completion of the present invention.

Specifically, the invention (1) provides an aminosilane compound represented by the following formula (1), $$R^1_2Si(NHR^2)_2 \qquad (1)$$

wherein $R^1$ represents a linear or branched alkyl group having 3 to 5 carbon atoms or a cyclopentyl group, two Ws being either the same or different, and $R^2$ represents a methyl group or an ethyl group.

The present invention further provides a catalyst component for olefin polymerization represented by the following formula (2), $$R^3_nSi(NR^4R^5)_{4-n} \qquad (2)$$

wherein $R^3$ represents a linear or branched alkyl group having 1 to 20 carbon atoms, a cycloalkyl group or a derivative thereof, a vinyl group, an aryl group, or an aralkyl group, two or more $R^3$s which may be present being either the same or different; $R^4$ represents a hydrogen atom, a linear or branched alkyl group having 1 to 20 carbon atoms, a cycloalkyl group or a derivative thereof, a vinyl group, an aryl group, or an aralkyl group, two or more $R^4$s which may be present being either the same or different; $R^5$ represents a linear or branched alkyl group having 1 to 20 carbon atoms, a cycloalkyl group or a derivative thereof, a vinyl group, an aryl group, or an aralkyl group, two or more $R^5$s which may be present being either the same or different; $R^4$ and $R^5$ may bond to form a ring; n is 0 or an integer from 1 to 3; and at least one of the $NR^4R^5$ groups is a secondary amino group.

The present invention further provides a catalyst for olefin polymerization formed from an aminosilane compound represented by the following formula (2) as an essential component, $$R^3_nSi(NR^4R^5)_{4-n} \qquad (2)$$

wherein $R^3$ represents a linear or branched alkyl group having 1 to 20 carbon atoms, a cycloalkyl group or a derivative thereof, a vinyl group, an aryl group, or an aralkyl group, two or more $R^3$s which may be present being either the same or different; $R^4$ represents a hydrogen atom, a linear or branched alkyl group having 1 to 20 carbon atoms, a cycloalkyl group or a derivative thereof, a vinyl group, an aryl group, or an aralkyl group, two or more $R^4$s which may be present being either the same or different; $R^5$ represents a linear or branched alkyl group having 1 to 20 carbon atoms, a cycloalkyl group or a derivative thereof, a vinyl group, an aryl group, or an aralkyl group, two or more $R^5$s which may be present being either the same or different; $R^4$ and $R^5$ may bond to form a ring; n is 0 or an integer from 1 to 3; and at least one of the $NR^4R^5$ groups is a secondary amino group.

Moreover, the present invention provides a process for producing an olefin polymer, wherein polymerization of an olefin is carried out in the presence of the catalyst for olefin polymerization.

The novel aminosilane compound and the specific aminosilane compound of the present invention, when used as a catalyst component for olefin polymerization, can maintain a higher stereoregularity and yield of the polymer than commonly used catalysts, and can produce a polymer having a high melt flow rate with a small amount of added hydrogen (hereinafter referred to as "hydrogen response"). Therefore, owing to the capability of reducing the amount of hydrogen used for the polymerization and high catalyst activity, the catalyst is expected not only to produce polyolefins for common use at a low cost, but also to be useful in the manufacture of olefin polymers having high functions.

BRIEF DESCRIPTION OF THE DRAWING

FIG. 1 is a flowchart showing a process for preparing the catalyst component and polymerization catalyst of the present invention.

BEST MODE FOR CARRYING OUT THE INVENTION

As examples of the novel aminosilane compound of the present invention, compounds represented by the above-mentioned formula (1) can be given and as examples thereof, bis(ethylamino)dicylcopentylsilane, bis(ethylamino)diisopropylsilane, and bis(methylamino)di-t-butylsilane can be given.

The process for synthesizing the aminosilane compound of the present invention is explained. A primary amino compound such as methylamine or ethylamine in a solvent is prepared in a flask under an inert gas atmosphere. As the solvent, a cyclic ether, a dialkyl ether, toluene, or a mixture of these solvents can be given. The solution prepared in the flask is cooled to −50 to 10° C., and an ether solution of a commercially available Grignard reagent in an amount equimolar to the primary amino compound or a hydrocarbon solution of alkyllithium in an amount equimolar to the primary amino compound is added dropwise to the cooled primary amino compound solution using a dropping funnel while stirring.

After completion of the dropwise addition, the temperature is gradually increased and the reaction is carried out for several hours at a temperature of 40° C. or higher. In this reaction, one of the hydrogen atoms of the primary amine is converted to Mg or Li to form a respective metal salt, which is in a slurry state in most situations. Next, a dialkoxydialkylsilane compound (hereinafter DADAS compound) is dissolved in a solvent and added to a flask equipped with a stirrer under an inert gas atmosphere. The solution is cooled to −50 to 10° C. As examples of the solvent for dissolving the DADAS compound, a cyclic ether, a dialkyl ether, and toluene can be given. Next, while stirring the DADAS compound solution, the slurry of the primary amine metal salt prepared above is added dropwise thereto under an inert gas atmosphere. In this instance, the amount of the primary amine metal salt is adjusted to twice the number of moles of the DADAS compound. After completion of the dropwise addition, the temperature is gradually increased and the reaction is carried out for several hours at a temperature of 40° C. or higher. After the reaction, the generated solid component comprising a metal alkoxide is separated from the solvent by filtering under an inert gas atmosphere or by a centrifugal separation process, the solid component is washed, and the wash liquid is added to the solution portion. The solvent component in the solution portion is evaporated under normal pressure or under reduced pressure in an inert gas atmosphere, and the main reaction product is purified by reduced pressure distillation. Other than the above-mentioned reaction solvents, hydrocarbon solvents such as cyclohexane, heptane, and hexane and a mixed solvent of the above-mentioned solvents can be used. The structure of the obtained aminosilane compound can be determined by identification using a well-known analysis method.

As the catalyst component for olefin polymerization of the present invention, a compound represented by the above-mentioned formula (2) can be used. The aminosilane compound is a compound having a nitrogen atom directly bonded to a silicon atom. In formula (2), when n is 1 or 2, $R^3$ is preferably a linear or branched alkyl group having 1 to 12 carbon atoms or a cycloalkyl group, two or more $R^3$s which may be present being either the same or different; $R^4$ is preferably a hydrogen atom; and $R^5$ is preferably a linear or branched alkyl group having 1 to 3 carbon atoms. Also, in formula (2), when n is 0, two out of the four $NR^4R^5$ groups are preferably dialkylamino groups, perhydroquinolino groups, or perhydroisoquinolino groups, or one out of the four $NR^4R^5$ groups is preferably a secondary amino group wherein the $R^4$ thereof is a hydrogen atom. In formula (2), the cycloalkyl derivative is a cycloalkyl group having a substituent and specifically, an alkyl-substituted cyclopentyl group, an alkyl-substituted cyclohexyl group, and an alkyl-substituted cycloheptyl group can be given as examples.

As examples of the aminosilane compound shown by the above-mentioned formula (2), (alkylamino)trialkylsilane, (alkylamino)dialkylcycloalkylsilane, (alkylamino)alkyldicycloalkylsilane, (alkylamino)tricycloalkylsilane, (alkylamino)(dialkylamino)dialkylsilane, (alkylamino)(dialkylamino)dicycloalkylsilane, bis(alkylamino)dialkylsilane, bis(alkylamino)alkylcycloalkylsilane, bis(alkylamino)dicycloalkylsilane, bis(alkylamino)(dialkylamino)alkylsilane, bis(alkylamino)(dialkylamino)cycloalkylsilane, di(alkylamino)dialkylsilane, di(alkylamino)alkylcycloalkylsilane, di(alkylamino)dicycloalkylsilane, di(cycloalkylamino)dialkylsilane, di(cycloalkylamino)alkylcycloalkylsilane, di(cycloalkylamino)dicycloalkylsilane, tris(alkylamino)alkylsilane, tris(alkylamino)cycloalkylsilane, tri(alkylamino)alkylsilane, tri(alkylamino)cycloalkylsilane, tri(cycloalkylamino)alkylsilane, tri(cycloalkylamino)cycloalkylsilane, tetrakis(alkylamino)silane, tris(alkylamino)dialkylaminosilane, tris(cycloalkylamino)dialkylaminosilane, bis(dialkylamino)bis(alkylamino)silane, dialkylaminotris(alkylamino)silane, bis(perhydroisoquinolino)bis(alkylamino)silane, bis(perhydroquinolino)bis(alkylamino)silane, bis(cycloalkylamino)bis(alkylamino)silane, tetra(alkylamino)silane, tri(alkylamino)dialkylaminosilane, tri(cycloalkylamino)dialkylaminosilane, di(dialkylamino)di(alkylamino)silane, dialkylaminotri(alkylamino)silane, di(alkyl-substituted-perhydroisoquinolino)di(alkylamino)silane, di(alkyl-substituted-perhydroisoquinolino)di(alkylamino)silane, and di(cycloalkylamino)di(alkylamino)silane can be given.

Among these compounds, bis(alkylamino)dicyclopentylsilane, bis(alkylamino)diisopropylsilane, bis(alkylamino)di-t-butylsilane, bis(alkylamino)-t-butylethylsilane, bis(alkylamino)-t-butylmethylsilane, bis(alkylamino)dicyclohexylsilane, bis(alkylamino)cyclohexylmethylsilane, bis(alkylamino)bis(decahydronaphtyl)silane, bis(alkylamino)cyclopentylcyclohexylsilane, bis(perhydroisoquinolino)(alkylamino)alkylsilane, bis(perhydroquinolino)(alkylamino)alkylsilane, di(alkylamino)dicyclopentylsilane, di(alkylamino)diisopropylsilane, di(alkylamino)di-t-butylsilane, di(alkylamino)-t-butylethylsilane, di(alkylamino)-t-butylmethylsilane, di(alkylamino)dicyclohexylsilane, di(alkylamino)cyclohexylmethylsilane, di(alkylamino)di(decahydronaphthyl)silane, di(alkylamino)cyclopentylcyclohexylsilane, di(alkylamino)cyclohexylthexylsilane, tetrakis(methylamino)silane, tris(alkylamino)alkylsilane, tris(alkylamino)cycloalkylsilane, bis(dialkylamino)bis(alkylamino)silane, dialkylaminotris(alkylamino)silane, and bis(perhydroisoquinolino)bis(alkylamino)silane are more preferable, with still more preferable compounds being bis(alkylamino)dicyclopentylsilane, bis(alkylamino)diisopropylsilane, bis(alkylamino)di-t-butylsilane, bis(alkylamino)-t-butylethylsilane, bis(alkylamino)-t-butylmethylsilane, bis(alkylamino)dicyclohexylsilane, bis(alkylamino)cyclohexylmethylsilane, bis(alkylamino)bis(decahydronaphthyl)silane, bis(alkylamino)cyclopentylcyclohexylsilane, bis(perhydroisoquinolino)(alkylamino)alkylsilane, and bis(perhydroquinolino)(alkylamino)alkylsilane.

Specific examples of the above-mentioned aminosilane compound include tris(methylamino)methylsilane, tris(methylamino)ethylsilane, tris(methylamino)n-propylsilane, tris(methylamino)isopropylsilane, tris(methylamino)n-butylsilane, tris(methylamino)isobutylsilane, tris(methylamino)t-butylsilane, tris(methylamino)cyclopentylsilane, tris(methylamino)cyclohexylsilane, tris(methylamino)vinylsilane, tris(ethylamino)methylsilane, tris(ethylamino)ethylsilane, tris(ethylamino)n-propylsilane, tris(ethylamino)isopropylsilane, tris(ethylamino)n-butylsilane, tris(ethylamino)isobutylsilane, tris(ethylamino)cyclopentylsilane, tris(ethylamino)cyclohexylsilane, tris(ethylamino)vinylsilane, tris(ethylamino)phenylsilane, tris(n-propylamino)methylsilane, tris(n-propylamino)ethylsilane, tris(n-propylamino)n-propylsilane, tris(n-propylamino)isopropylsilane, tris(n-propylamino)n-butylsilane, tris(n-propylamino)isobutylsilane, tris(n-propylamino)cyclopentylsilane, tris(n-propylamino)cyclohexylsilane, tris(n-propylamino)vinylsilane, tris(isopropylamino)methylsilane, tris(isopropylamino)ethylsilane, tris(isopropylamino)n-propylsilane, tris(isopropylamino)isopropylsilane, tris(isopropylamino)n-butylsilane, tris(isopropylamino)isobutylsilane, tris(isopropylamino)cyclopentylsilane, tris(isopropylamino)cyclohexylsilane, tris(isopropylamino)vinylsilane, tris(n-butylamino)isopropylsilane, tris(sec-butylamino)ethylsilane, tris(t-butylamino)methylsilane, tris(cyclopentylamino)ethylsilane, tris(cyclopentylamino)isopropylsilane, tris(cyclohexylamino)ethylsilane, tris(cyclohexylamino)isopropylsilane, tris(cyclohexylamino)benzylsilane, tris(cyclohexylamino)phenylsilane, tris(cyclohexylamino)vinylsilane, bis(methylamino)(dimethylamino)methylsilane, bis(methylamino)(diethylamino)methylsilane, bis(methylamino)(methylethylamino)methylsilane, bis(methylamino)(di-n-propylamino)methylsilane, bis(methylamino)(methyl-n-propylamino)methylsilane, bis(methylamino)(methylisopropylamino)methylsilane, bis(methylamino)(methyl-n-butylamino)methylsilane, bis(methylamino)(ethyl-n-butylamino)methylsilane, bis(methylamino)(ethylisobutylamino)methyl bis(methylamino)(ethyl-sec-butylamino)methylsilane, bis(methylamino)(ethyl-t-butylamino)methylsilane, bis(methylamino)(methylcyclopentylamino)methylsilane, bis(methylamino)(ethylcyclopentylamino)methylsilane, bis(methylamino)(methylcyclohexylamino)methylsilane, bis(methylamino)(ethylcyclohexylamino)methylsilane, bis(methylamino)(dimethylamino)ethylsilane, bis(methylamino)(diethylamino)ethylsilane, bis(methylamino)(methylethylamino)ethylsilane, bis(methylamino)(di-n-propylamino)ethylsilane, bis(methylamino)(methyl-n- propylamino)ethylsilane, bis(methylamino)(methylisopropylamino)ethylsilane, bis(methylamino)(methyl-n-butylamino)ethylsilane, bis(methylamino)(ethyl-n-butylamino)ethylsilane, bis(methylamino)(ethylisobutylamino)ethylsilane, bis(methylamino)(ethyl-sec-butylamino)ethylsilane, bis(methylamino)(ethyl-t-butylamino)ethylsilane, bis(methylamino)(methylcyclopentylamino)ethylsilane, bis(methylamino)(ethylcyclopentylamino)ethylsilane, bis(methylamino)(methylcyclohexylamino)ethylsilane, bis(methylamino)(ethylcyclohexylamino)ethylsilane, bis(methylamino)(isobutylamino)methylsilane, bis(methylamino)(isobutylamino)ethylsilane, bis(methylamino)(isobutylamino)n-propylsilane, bis(methylamino)(isobutylamino)isopropylsilane, bis(methylamino)(isobutylamino)n-butylsilane, bis(methylamino)(isobutylamino)sec-butylsilane, bis(methylamino)(isobutylamino)isobutylsilane, bis(methylamino)(isobutylamino)t-butylsilane, bis(methylamino)(isobutylamino)thexylsilane, bis(methylamino)(isobutylamino)cyclopentylsilane, bis(methylamino)(isobutylamino)cyclohexylsilane, bis(methylamino)(isobutylamino)perhydronaphthylsilane, bis(methylamino)(isobutylamino)adamantylsilane, bis(methylamino)(t-butylamino)methylsilane, bis(methylamino)(t-butylamino)ethylsilane, bis(methylamino)(t-butylamino)n-propylsilane, bis(methylamino)(t-butylamino)isopropylsilane, bis(methylamino)(t-butylamino)n-butylsilane, bis(methylamino)(t-butylamino)sec-butylsilane, bis(methylamino)(t-butylamino)isobutylsilane, bis(methylamino)(t-butylamino)t-butylsilane, bis(methylamino)(t-butylamino)thexylsilane, bis(methylamino)(t-butylamino)cyclopentylsilane, bis(methylamino)(t-butylamino)cyclohexylsilane, bis(methylamino)(t-butylamino)perhydronaphthylsilane, bis(methylamino)(t-butylamino)adamantylsilane, bis(methylamino)dimethylsilane, bis(methylamino)diethylsilane, bis(methylamino)divinylsilane, bis(methylamino)di-n-propylsilane, bis(methylamino)diisopropylsilane, bis(methylamino)di-n-butylsilane, bis(methylamino)diisobutylsilane, bis(methylamino)di-sec-butylsilane, bis(methylamino)di-t-butylsilane, bis(methylamino)di-n-neopentylsilane, bis(methylamino)dicyclopentylsilane, bis(methylamino)dicyclohexylsilane, bis(methylamino)di-4-methoxyphenylsilane, bis(methylamino)methylethylsilane, bis(methylamino)methyl-t-butylsilane, bis(methylamino)m-ethylphenylsilane, bis(methylamino)ethyl-t-butylsilane, bis(methylamino)sec-butylmethylsilane, bis(methylamino)sec-butylethylsilane, bis(methylamino)methylcyclopentylsilane, bis(methylamino)ethylcyclopentylsilane, bis(methylamino)cyclopentylcyclohexylsilane, bis(methylamino)methylcyclohexylsilane, bis(methylamino)didecahydronaphthylsilane, bis(methylamino)thexylmethylsilane, bis(ethylamino)dimethylsilane, bis(ethylamino)diethylsilane, bis(ethylamino)divinylsilane, bis(ethylamino)di-n-propylsilane, bis(ethylamino)diisopropylsilane, bis(ethylamino)di-n-butylsilane, bis(ethylamino)diisobutylsilane, bis(ethylamino)di-sec-butylsilane, bis(ethylamino)di-t-butylsilane, bis(ethylamino)dicyclopentylsilane, bis(ethylamino)dicyclohexylsilane, bis(ethylamino)didecahydronaphthylsilane, bis(ethylamino)methylethylsilane, bis(ethylamino)methyl-t-butylsilane, bis(ethylamino)methylphenylsilane, bis(ethylamino)ethyl-t-butylsilane, bis(ethylamino)sec-butylmethylsilane, bis(ethylamino)sec-butylethylsilane, bis(ethylamino)methylcyclopentylsilane, bis(ethylamino)cyclopentylcyclohexylsilane, bis(ethylamino)methylcyclohexylsilane, bis(ethylamino)t-butylisobutylsilane, bis(ethylamino)cyclohexylthexylsilane, bis(n-propylamino)dimethylsilane, bis(n-propylamino)diethylsilane, bis(n-propylamino)divinylsilane, bis(n-propylamino)di-n-propylsilane, bis(n-propylamino)diisopropylsilane, bis(n-propylamino)di-n-butylsilane, bis(n-propylamino)diisobutylsilane, bis(n-propylamino)di-sec-butylsilane, bis(n-propylamino)di-t-butylsilane, bis(n-propylamino)di-n-neopentylsilane, bis(n-propylamino)dicyclopentylsilane, bis(n-propylamino)dicyclohexylsilane, bis(isopropylamino)dimethylsilane, bis(isopropylamino)diethylsilane, bis(isopropylamino)divinylsilane, bis(isopropylamino)di-n-propylsilane, bis(isopropylamino)diisopropylsilane, bis(isopropylamino)di-n-butylsilane, bis(isopropylamino)diisobutylsilane, bis(isopropylamino)di-sec-butylsilane, bis(isopropylamino)di-t-butylsilane, bis(isopropylamino)dineopentylsilane, bis(isopropylamino)dicyclopentylsilane, bis(isopropylamino)dicyclohexylsilane, bis(isopropylamino)didecahydronaphthylsilane, bis(isopropylamino)ditetrahydronaphthylsilane, bis(isopropylamino)dibenzylsilane, bis(isopropylamino)diphenylsilane, bis(isopropylamino)methylethylsilane, bis(isopropylamino)methyl-t-butylsilane, bis(isopropylamino)ethyl-t-butylsilane, bis(isopropylamino)sec-butylmethylsilane, bis(isopropylamino)sec-butylethylsilane, bis(isopropylamino)methylneopentylsilane, bis(isopropylamino)methylcyclopentylsilane, bis(isopropylamino)isopropylcyclopentylsilane, bis(isopropylamino)isobutylcyclopentylsilane, bis(isopropylamino)cyclopentylcyclohexylsilane, bis(isopropylamino)methylcyclohexylsilane, tetrakis(methylamino)silane, tetrakis(ethylamino)silane, tetrakis(n-propylamino)silane, tetrakis(isopropylamino)silane, tetrakis(n-butylamino)silane, tetrakis(isobutylamino)silane, tetrakis(sec-butylamino)silane, tetrakis(n-hexylamino)silane, tris(methylamino)(ethylamino)silane, tris(methylamino)(n-propylamino)silane, tris(methylamino)(isopropylamino)silane, tris(methylamino)(n-butylamino)silane, tris(methylamino)(sec-butylamino)silane, tris(methylamino)(t-butylamino)silane, tris(methylamino)(neo-pentylamino)silane, tris(methylamino)(di-4-methoxyphenylamino)silane, tris(methylamino)(diethylamino)silane, tris(methylamino)(diisopropylamino)silane, tris(methylamino)(diisobutylamino)silane, tris(methylamino)(di-sec-butylamino)silane, tris(methylamino)(di-t-butylamino)silane, tris(methylamino)(perhydroisoquinolino)silane, tris(methylamino)(perhydroquinolino)silane, tris(methylamino)(dicyclopentylamino)silane, tris(methylamino)(dicyclohexylamino)silane, tris(methylamino)(t-butylethylamino)silane, tris(methylamino)(t-butyl-n-propylamino)silane, tris(methylamino)(sec-butylethylamino)silane, tris(methylamino)(sec-butylisopropylamino)silane, tris(ethylamino)(methylamino)silane, tris(ethylamino)(n-propylamino)silane, tris(ethylamino)(isopropylamino)silane, tris(ethylamino)(n-butylamino)silane, tris(ethylamino)(sec-butylamino)silane, tris(ethylamino)(t-butylamino)silane, tris(ethylamino)(neopentylamino)silane, tris(ethylamino)(diethylamino)silane, tris(ethylamino)(diisopropylamino)silane, tris(ethylamino)(diisobutylamino)silane, tris(ethylamino)(di-sec-butylamino)silane, tris(ethylamino)(di-t-butylamino)silane, tris(ethylamino)(dicyclopentylamino)silane, tris(ethylamino)(dicyclohexylamino)silane, tris(ethylamino)(perhydroisoquinolino)silane, tris(ethylamino)(perhydroquinolino)silane, tris(ethylamino)(t-butylethylamino)silane, tris(n-propylamino)(methylamino)silane, tris(n-propyl)(isopropylamino)silane, tris(n-propylamino)(t-butylamino)silane, tris(n-propylamino)(n-butylamino)silane, tris(n-propylamino)(sec-butylamino)

silane, tris(n-propylamino)(cyclopentylamino)silane, tris(n-propylamino)(cyclohexylamino)silane, tris(n-propylamino)(diethylamino)silane, tris(n-propylamino)(diisopropylamino)silane, tris(n-propylamino)(diisobutylamino)silane, tris(n-propylamino)(di-t-butylamino)silane, tris(n-propylamino)(dicyclopentylamino)silane, tris(n-propylamino)(dicyclohexylamino)silane, tris(n-propylamino)(perhydroisoquinolino)silane, tris(n-propylamino)(perhydroquinolino)silane, bis(methylamino)bis(ethylamino)silane, bis(methylamino)bis(n-propylamino)silane, bis(methylamino)bis(isopropylamino)silane, bis(methylamino)bis(n-butylamino)silane, bis(methylamino)bis(isobutylamino)silane, bis(methylamino)bis(sec-butylamino)silane, bis(methylamino)bis(t-butylamino)silane, bis(methylamino)bis(cyclopentylamino)silane, bis(methylamino)bis(cyclohexylamino)silane, bis(methylamino)bis(perhydroisoquinolino)silane, bis(methylamino)bis(tetrahydroisoquinolino)silane, bis(methylamino)bis(perhydroquinolino)silane, bis(methylamino)bis(diethylamino)silane, bis(methylamino)bis(di-n-propylamino)silane, bis(methylamino)bis(diisopropylamino)silane, bis(methylamino)bis(di-n-butylamino)silane, bis(methylamino)bis(diisobutylamino)silane, bis(methylamino)bis(di-sec-butylamino)silane, bis(methylamino)bis(di-t-butylamino)silane, bis(methylamino)bis(dicyclopentylamino)silane, bis(methylamino)bis(dicyclohexylamino)silane, bis(ethylamino)bis(n-propylamino)silane, bis(ethylamino)bis(isopropylamino)silane, bis(ethylamino)bis(n-butylamino)silane, bis(ethylamino)bis(isobutylamino)silane, bis(ethylamino)bis(sec-butylamino)silane, bis(ethylamino)bis(t-butylamino)silane, bis(ethylamino)bis(cyclopentylamino)silane, bis(ethylamino)bis(cyclohexylamino)silane, bis(ethylamino)bis(perhydroisoquinolino)silane, bis(ethylamino)bis(perhydroquinolino)silane, bis(ethylamino)bis(cyclooctamethyleneimino)silane, bis(ethylamino)bis(diethylamino)silane, bis(ethylamino)bis(di-n-propylamino)silane, bis(ethylamino)bis(diisopropylamino)silane, bis(ethylamino)bis(di-n-butylamino)silane, bis(ethylamino)bis(diisobutylamino)silane, bis(ethylamino)bis(di-sec-butylamino)silane, bis(ethylamino)bis(di-t-butylamino)silane, bis(ethylamino)bis(dicyclopentylamino)silane, bis(ethylamino)bis(dicyclohexylamino)silane, bis(n-propylamino)bis(cyclopentylamino)silane, bis(n-propylamino)bis(cyclohexylamino)silane, bis(n-propylamino)bis(perhydroisoquinolino)silane, bis(n-propylamino)bis(perhydroisoquinolino)silane, bis(n-propylamino)bis(perhydroquinolino)silane, bis(n-propylamino)bis(diethylamino)silane, bis(propylamino)bis(di-n-propylamino)silane, bis(n-propylamino)bis(diisopropylamino)silane, bis(n-propylamino)bis(di-n-butylamino)silane, bis(n-propylamino)bis(diisobutylamino)silane, bis(n-propylamino)bis(di-sec-butylamino)silane, bis(n-propylamino)bis(di-t-butylamino)silane, bis(n-propylamino)bis(dicyclopentylamino)silane, bis(n-propylamino)bis(dicyclohexylamino)silane, tris(dimethylamino)(methylamino)silane, tris(diethylamino)(methylamino)silane, tris(di-n-propylamino)(methylamino)silane, tris(diisopropylamino)(methylamino)silane, tris(di-n-butylamino)(methylamino)silane, tris(diisobutylamino)(methylamino)silane, tris(t-butylamino)(methylamino)silane, tris(cyclopentylamino)(methylamino)silane, tris(cyclohexylamino)(methylamino)silane, tris(dimethylamino)(ethylamino)silane, tris(diethylamino)(ethylamino)silane, tris(di-n-propylamino)(ethylamino)silane, tris(diisopropylamino)(ethylamino)silane, tris(di-n-butylamino)(ethylamino)silane, tris(diisobutylamino)(ethylamino)silane, tris(t-butylamino)(ethylamino)silane, tris(cyclopentylamino)(ethylamino)silane, tris(cyclohexylamino)(ethylamino)silane, tris(dimethylamino)(n-propylamino)silane, tris(diethylamino)(n-propylamino)silane, tris(di-n-propylamino)(n-propylamino)silane, tris(diisopropylamino)(n-propylamino)silane, tris(di-n-butylamino)(n-propylamino)silane, tris(diisobutylamino)(n-propylamino)silane, tris(t-butylamino)(n-propylamino)silane, tris(cyclopentylamino)(n-propylamino)silane, and tris(cyclohexylamino)(n-propylamino)silane.

The compound represented by the above-mentioned formula (2) can be easily synthesized by a known synthesis method such as a chlorine exchange method, a method using an organolithium compound, or a method using a Grignard reagent or by a combination of these methods. As an example of a synthesis method of bis(alkylamino)dicyclopentylsilane among the aminosilane compounds of the present invention, a reaction of dicyclopentyldialkoxysilane with twice the number of moles of a Li salt of an alkylamine or a Mg salt of an alkylamine can be given. As examples of the solvent, ether compounds such as THF and dialkyl ether, aromatic compounds such as toluene, saturated hydrocarbon compounds such as pentane, hexane, heptane, and cyclohexane, and a mixture of these solvents can be given. Also, in formula (2), when $R^3$ is an alkylamine, the amount of the metal salt of a primary amine is adjusted to the number of the alkoxy group in the $(alkoxy)_n(alkyl)_{4-n}$ silane compound, that is, to 1 to 4 times the numbers of moles the $(alkoxy)_n(alkyl)_{4-n}$ silane compound.

The catalyst for olefin polymerization of the present invention is formed using the aminosilane compound represented by the above-mentioned formula (2) as an essential component. As specific examples of preferable compounds of formula (2) for forming the catalyst for olefin polymerization of the present invention, the same compounds as given in the description of formula (2) for the catalyst component for olefin polymerization can be given. In addition to the aminosilane compounds represented by the above-mentioned formula (2), the catalyst for olefin polymerization of the present invention can be formed using (A) a solid catalyst component comprising magnesium, titanium, a halogen, and an electron-donor compound and (B) an organoaluminum compound represented by the following formula (3),

$$R^6_p AlQ_{3-p} \qquad (3)$$

wherein $R^6$ represents an alkyl group having 1 to 4 carbon atoms, Q represents a hydrogen atom or a halogen atom, and p represents a real number satisfying the formula $0 < p \le 3$.

Among the components of the catalyst for olefin polymerization of the present invention, the solid catalyst component (A) (hereinafter referred to as "component (A)" from time to time), which comprises magnesium, titanium, a halogen, and an electron donor compound, can be obtained by causing (a) a magnesium compound, (b) a tetravalent titanium halogen compound, and (c) an electron donor compound to come in contact with each other. As examples of the magnesium compound (hereinafter simple referred to as "component (a)" from time to time), a magnesium dihalide, a dialkylmagnesium, an alkylmagnesium halide, a dialkoxymagnesium, a diaryloxymagnesium, an alkoxymagnesium halide, and a fatty acid magnesium can be given. Among these magnesium compounds, a magnesium dihalide, a mixture of magnesium dihalide and dialkoxymagnesium, and a dialkoxymagnesium are preferable, and a dialkoxymagnesium is particularly preferable. As specific examples, dimethoxymagnesium, diethoxymagnesium, dipropoxymagnesium, dibutoxymagnesium, ethoxymethoxymagnesium, ethoxypropxymagnesium, and butoxyethoxymagnesium can be given. Diethoxymagnesium is particularly preferable.

Also, these dialkoxymagnesium may be obtained by reacting metallic magnesium with an alcohol in the presence of a halogen-containing metal compound or the like. The dialkoxymagnesium may be used alone or in combination or two or more.

The dialkoxymagnesium compound used is preferably in the form of granules or a powder and either amorphous or spherical in the configuration. For example, when a spherical dialkoxymagnesium is used, a polymer powder having a better particle shape and a narrower particle size distribution can be obtained. This improves handling operability of the produced polymer powder during the polymerization operation and eliminates problems such as clogging of the filter or the like in the polymer separation device caused by fine particles contained in produced polymer powder.

The spherical dialkoxymagnesium need not necessarily be completely spherical, but may be oval or potato-shaped. Specifically, the particles may have a ratio (L/W) of the major axis diameter (L) to the minor axis diameter (W) usually of 3 or less, preferably of 1 to 2, and more preferably of 1 to 1.5.

Dialkoxymagnesium with an average particle size from 1 to 200 µm can be used. A more preferable average particle size is 5 to 150 µm. In the case of spherical dialkoxymagnesium, the average particle size is usually from 1 to 100 µm, preferably from 5 to 50 µm, and more preferably from 10 to 40 µm. A powder having a narrow particle size distribution with a small fine and coarse powder content is preferably used. Specifically, the content of particles with a diameter of 5 µm or less should be 20% or less, and preferably 10% or less. On the other hand, the content of particles with a diameter of 100 µm or more should be 10% or less, and preferably 5% or less. Moreover, the particle size distribution represented by (D90/D10), wherein D90 is a particle size of 90% of the integrated particle size and D10 is a particle size of 10% of the integrated particle size, is 3 or less, and preferably 2 or less.

Methods for producing such spherical dialkoxymagnesium are described in, for example, Japanese Patent Applications Laid-open No. 58-4132, No. 62-51633, No. 3-74341, No. 4-368391, and No. 8-73388.

The tetravalent titanium halide compound (b) (hereinafter referred to from time to time as "component (b)") used for the preparation of the component (A) in the present invention is one or more compounds selected from the group consisting of a titanium halide or alkoxytitanium halide represented by the formula $Ti(OR^7)_nX_{4-n}$, wherein $R^7$ represents an alkyl group having 1 to 4 carbon atoms, X represents a halogen atom, and n represents an integer satisfying the formula $0 \leq n \leq 4$.

Specific examples include, as titanium halides, titanium tetrahalides such as titanium tetrachloride, titanium tetrabromide, and titanium tetraiodide and, as alkoxytitanium halides, methoxytitanium trichloride, ethoxytitanium trichloride, propoxytitanium trichloride, n-butoxytitanium trichloride, dimethoxytitanium dichloride, diethoxytitanium dichloride, dipropoxytitanium dichloride, di-n-butoxytitanium dichloride, trimethoxytitanium chloride, triethoxytitanium chloride, tripropoxytitanium chloride, and tri-n-butoxy titanium chloride. Of these, titanium tetrahalides are preferable, with titanium tetrachloride being particularly preferable. These titanium compounds may be used either individually or in combination of two or more.

The electron donor compound (hereinafter referred to from time to time as "component (c)") used for preparing the solid catalyst component (A) is an organic compound containing an oxygen atom or a nitrogen atom. Alcohols, phenols, ethers, esters, ketones, acid halides, aldehydes, amines, amides, nitriles, isocyanates, and organosilicon compounds containing an Si—O—C bond or an Si—N—C bond can be given as examples.

As specific examples, alcohols such as methanol, ethanol, n-propanol, 2-ethylhexanol; phenols such as phenol and cresol; ethers such as dimethyl ether, diethyl ether, dipropyl ether, dibutyl ether, diamyl ether, diphenyl ether, 9,9-bis (methoxymethyl)fluorene, and 2-isopropyl-2isopentyl-1,3-dimethoxy propane; monocarboxylic acid esters such as methyl formate, ethyl acetate, vinyl acetate, propyl acetate, octyl acetate, cyclohexyl acetate, ethyl propionate, ethyl butylate, ethyl benzoate, propyl benzoate, butyl benzoate, octyl benzoate, cyclohexyl benzoate, phenyl benzoate, methyl p-toluate, ethyl p-toluate, methyl anisate, and ethyl anisate; dicarboxylic acid esters such as diethyl malonate, dipropyl malonate, dibutyl malonate, diisobutyl malonate, dipentyl malonate, dineopentyl malonate, diethyl isopropylbromomalonate, diethyl butylbromomalonate, diethyl diisobutylbromomalonate, diethyl diisopropylmalonate, diethyl dibutylmalonate, diethyl diisobutylmalonate, diethyl diisopentylmalonate, diethyl isopropylbutylmalonate, dimethyl isopropylisopentylmalonate, diethyl bis(3-chloro-n-propyl)malonate, diethyl bis(3-bromo-n-propyl)malonate, diethyl maleate, dibutyl maleate, dimethyl 2,3-di-n-propyl-succinate, diethyl 2,3-di-n-propylsuccinate, dipropyl 2,3-di-n-propylsuccinate, dimethyl adipate, diethyl adipate, dipropyl adipate, dibutyl adipate, diisodecyl adipate, dioctyl adipate, phthalic acid diesters, and phthalic acid diester derivatives; ketones such as acetone, methyl ethyl ketone, methyl butyl ketone, acetophenone, and benzophenone; acid chlorides such as phthalic acid dichloride and terephthalic acid dichloride; aldehydes such as acetaldehyde, propylaldehyde, octylaldehyde, and benzaldehyde; amines such as methylamine, ethylamine, tributylamine, piperidine, aniline, and pyridine; amides such as oleic amide and stearic amide; nitriles such as acetonitrile, benzonitrile, and tolylnitrile; isocyanates such as methyl isocyanate and ethyl isocyanate; organosilicon compounds containing an Si—O—C bond such as phenylalkoxysilane, alkylalkoxysilane, phenylalkylalkoxysilane, cycloalkylalkoxysilane, and cycloalkylalkylalkoxysilane, and organosilicon compounds having a Si—N—C bond such as bis(alkylamino)dialkoxysilane, bis (cycloalkylamino)dialkoxysilane, alkyl(alkylamino)dialkoxysilane, dialkylaminotrialkoxysilane, and cycloalkylaminotrialkoxysilane can be given.

Among the above electron donor compounds, the esters, particularly aromatic dicarboxylic acid diesters, are preferably used. Phthalic acid diesters and phthalic acid diester derivatives are ideal compounds. Specific examples of the phthalic acid diester include the following compounds: dimethyl phthalate, diethyl phthalate, di-n-propyl phthalate, diisopropyl phthalate, di-n-butyl phthalate, diisobutyl phthalate, ethylmethyl phthalate, methylisopropyl phthalate, ethyl (n-propyl)phthalate, ethyl(n-butyl)phthalate, ethyl(isobutyl) phthalate, di-n-pentyl phthalate, diisopentyl phthalate, dineopentyl phthalate, dihexyl phthalate, di-n-heptyl phthalate, di-n-octyl phthalate, bis(2,2-dimethylhexyl)phthalate, bis(2-ethylhexyl)phthalate, di-n-nonyl phthalate, diisodecyl phthalate, bis(2,2-dimethylheptyl)phthalate, n-butyl(isohexyl)phthalate, n-butyl(2-ethylhexyl)phthalate, n-pentyl (hexyl)phthalate, n-pentyl(isohexyl)phthalate, isopentyl (heptyl)phthalate, n-pentyl(2-ethylhexyl)phthalate, n-pentyl (isononyl)phthalate, isopentyl(n-decyl)phthalate, n-pentyl (undecyl)phthalate, isopentyl(isohexyl)phthalate, n-hexyl(2, 2-dimethylhexyl)phthalate, n-hexyl(isononyl)phthalate, n-hexyl(n-decyl)phthalate, n-heptyl(2-ethylhexyl)phthalate, n-heptyl(isononyl)phthalate, n-heptyl(neodecyl)phthalate, and 2-ethylhexyl(isononyl)phthalate. One or more of these compounds can be used.

As examples of the phthalic acid diester derivatives, compounds in which one or two hydrogen atoms on the benzene ring to which the two ester groups of the phthalic diesters bond are replaced with an alkyl group having 1 to 5 carbon atoms or a halogen atom such as a chlorine atom, a bromine atom, and a fluorine atom can be given. The solid catalyst component prepared by using the phthalic acid diester derivatives as an electron donor compound can particularly contribute to a melt flow rate increase with a given amount of hydrogen by increasing hydrogen response, that is, can increase the melt flow rate of polymer by using the same or a smaller amount of hydrogen during the polymerization. As specific examples, dineopentyl 4-methylphthalate, dineopentyl 4-ethylphthalate, dineopentyl 4,5-dimethylphthalate, dineopentyl 4,5-diethylphthalate, diethyl 4-chlorophthalate, di-n-butyl 4-chlorophthalate, dineopentyl 4-chlorophthalate, diisobutyl 4-chlorophthalate, diisohexyl 4-chlorophthalate, diisooctyl 4-chlorophthalate, diethyl 4-bromophthalate, di-n-butyl 4-bromophthalate, dineopentyl 4-bromophthalate, diisobutyl 4-bromophthalate, diisohexyl 4-bromophthalate, diisooctyl 4-bromophthalate, diethyl 4,5-dichlorophthalate, di-n-butyl 4,5-dichlorophthalate, diisohexyl 4,5-dichlorophthalate, and diisooctyl 4,5-dichlorophthalate can be given. Of these, dineopentyl 4-bromophthalate, di-n-butyl 4-bromophthalate, and diisobutyl 4-bromophthalate are preferable.

The above ester compounds are preferably used in combination of two or more. In this instance, the esters are preferably combined so that the total carbon atom number in the alkyl group possessed by one ester may differ four or more from that possessed by another ester.

The aminosilane compounds shown by the formula (2) can also be used as the electron donor compound (c) (an internal donor) of the solid catalyst component (A). Specific examples of the aminosilane compounds shown by the formula (2) used as the internal donor are the same as those of the compounds shown by the formula (2) used for the catalyst component for olefin polymerization.

The component (A) of the present invention can be preferably prepared by causing the above components (a), (b), and (c) to come in contact with each other in the presence of an aromatic hydrocarbon compound (d) (hereinafter may be simply referred to as "component (d)"). Hydrocarbon compounds having a boiling point of 50 to 150° C. such as toluene, xylene, ethylbenzene, cyclohexane, and cyclohexene are preferably used as the component (d). These aromatic hydrocarbons can be used either individually or in combination of two or more.

As a preferable method for preparing the component (A) of the present invention, a method of preparing a suspension liquid of the component (a), the component (c), and the hydrocarbon compound (d) having a boiling point of 50 to 150° C., causing this suspension liquid to contact with a mixed solution made from the component (b) and the component (d), and reacting the mixture can be given.

In the preparation of the solid catalyst component (A) of the present invention, in addition to the above components, a polysiloxane (hereinafter may be simply referred to as "component (e)") can be preferably used to improve the stereoregularity or crystallinity of the formed polymer and to reduce the amount of fine polymer particles. Polysiloxanes are polymers having a siloxane bond (—Si—O bond) in the main chain and are generally referred to as silicone oil. The polysiloxanes used in the present invention are chain-structured, partially hydrogenated, cyclic or modified polysiloxanes which are liquid or viscous at normal temperatures with a viscosity at 25° C. in the range of 0.02 to 100 cm²/s (2 to 10,000 cSt).

As examples of the chain-structured polysiloxane, dimethylpolysiloxane and methylphenylpolysiloxane can be given; as examples of the partially hydrogenated polysiloxane, methyl hydrogen polysiloxanes with a hydrogenation degree of 10 to 80% can be given; as examples of the cyclic polysiloxane, hexamethylcyclotrisiloxane, octamethylcyclotetrasiloxane, decamethylcyclopentanesiloxane, 2,4,6-trimethylcyclotrisiloxane, 2,4,6,8-tetramethylcyclotetrasiloxane can be given; as examples of the modified polysiloxane, higher fatty acid group-substituted dimethylsiloxane, epoxy group-substituted dimethylsiloxane, and polyoxyalkylene group-substituted dimethylsiloxane can be given. Of these, decamethylcyclopentasiloxane and dimethylpolysiloxane are preferable, with decamethylcyclopentasiloxane being particularly preferable.

The component (A) in the present invention is prepared by causing the above components (a), (b), and (c), and, as required, the component (d) or component (e) to come in contact with each other. The method of preparing the component (A) will now be described in detail. One specific example of the method for preparing the component (A) comprises suspending the magnesium compound (a) in an alcohol, a halogenated hydrocarbon solvent, the tetravalent titanium halide (b), or the hydrocarbon compound (d), and causing the electron donor compound (c) such as a phthalic acid diester and/or the tetravalent titanium halide (b) to come in contact with the suspension. In this method, the component (A) in the form of spherical particles with a sharp particle size distribution can be obtained by using a spherical magnesium compound. Such a component (A) in the form of spherical particles with a sharp particle size distribution can also be obtained without using a spherical magnesium compound If particles are formed by a spray dry method in which a solution or a suspension liquid is sprayed and dried using a sprayer, for example.

These components are caused to come in contact with each other in a vessel equipped with a stirrer in an inert gas atmosphere from which water and the like have been removed while stirring. The contact temperature, which is a temperature when these components are caused to come into contact with each other, may be either the same as or different from the reaction temperature. When the components are caused to come into contact with each other by stirring for preparing the mixture or are dispersed or suspended for a denaturing treatment, the components may be stirred at a comparatively low temperature of around room temperature. A temperature in a range from 40 to 130° C. is preferable for obtaining the product by reaction after contact. The reaction does not sufficiently proceed at a reaction temperature below 40° C., resulting in a solid catalyst component with inadequate properties. On the other hand, control of the reaction becomes difficult at a temperature above 130° C. due to vaporization of the solvent and the like. The reaction time is one minute or more, preferably ten minutes or more, and still more preferably 30 minutes or more.

As preferable processes for preparing the component (A) of the present invention, a process comprising suspending the component (a) in the component (d), causing the resulting suspension to come in contact with the component (b), then the component (c) and component (d), and causing these components to react and a process comprising suspending the component (a) in the component (d), causing the resulting suspension liquid to come in contact with the component (c), then the component (b), and causing these components to react can be given. The component (A) thus prepared may be caused to come in contact with the component (b) or the components (b) and (c) once more or two or more times to improve the performance of the ultimate solid catalyst component. This contacting step is preferably carried out in the presence of the hydrocarbons (d).

As a preferable method for preparing the component (A) of the present invention, a method of preparing a suspension liquid of the component (a), the component (c), and the hydrocarbon compound (d) having a boiling point of 50 to 150° C., causing this suspension liquid to contact with a mixed solution made from the component (b) and the component (d), and reacting the mixture can be given.

As a preferable example of the method for preparing the component (A), the following methods can be given. A suspension is prepared from the above component (a), component (c), and a hydrocarbon compound (d) having a boiling point of 50 to 150° C. A mixed solution is prepared from the above component (c) and the hydrocarbon compound (d) having a boiling point of 50 to 150° C. The above-described suspension liquid is added to this solution. The resulting mixture is heated and reacted (a primary reaction). After the reaction, the solid product is washed with a hydrocarbon compound which is liquid at normal temperatures to obtain a solid product. Furthermore, an additional component (b) and the hydrocarbon compound (d) having a boiling point of 50 to 150° C. may be caused to come in contact with the washed solid product at a temperature of −20 to 100° C. The temperature is raised to react the mixture (a secondary reaction), and after the reaction, the reaction mixture is washed with a hydrocarbon compound which is liquid at normal temperatures one to ten times to obtain the component (A).

Based on the above description, a particularly preferable process for preparing the solid catalyst component (A) comprises suspending the dialkoxymagnesium compound (a) in the hydrocarbon compound (d) having a boiling point in the range of 50 to 150° C., causing the tetravalent titanium halide (b) to contact the suspension liquid, and reacting the mixture. In this instance, one or more electron donor compounds (c) such as phthalic acid diester are caused to come in contact with the suspension liquid at a temperature from −20 to 130° C., either before or after the tetravalent titanium halide compound (b) is contacted, then optionally, the component (e) is contacted and reacted to obtain a solid product (1). In this instance, it is desirable to carry out an aging reaction at low temperature either before or after the above one or more electron donor compounds are caused to come in contact with the suspension liquid. After washing the solid product (1) with a hydrocarbon compound which is liquid at normal temperatures (intermediate washing), the tetravalent titanium halide (b) is again caused to come contact and react with the solid product (1) in the presence of the hydrocarbon compound at a temperature of −20 to 100° C. to obtain a solid reaction product (2). As required, the intermediate washing and the reaction may be further repeated several times. Subsequently, the solid product (2) is washed with a liquid hydrocarbon compound by decantation at normal temperature to obtain the solid catalyst component (A).

The ratio of the components used for preparing the solid catalyst component (A) cannot be defined unconditionally, because such a ratio varies according to the method of preparation employed. For example, the tetravalent titanium halide (b) is used in an amount from 0.5 to 100 mol, preferably from 0.5 to 50 mol, still more preferably from 1 to 10 mol; the electron donor compound (c) is used in an amount from 0.01 to 10 mol, preferably from 0.01 to 1 mol, and still more preferably from 0.02 to 0.6 mol; the hydrocarbon compound (d) is used in an amount from 0.001 to 500 mol, preferably from 0.001 to 100 mol, and still more preferably from 0.005 to 10 mol; and the polysiloxane (e) is used in an amount of from 0.01 to 100 g, preferably from 0.05 to 80 g, and still more preferably from 1 to 50 g, for one mol of the magnesium compound (a).

Although there are no specific limitations to the amounts of titanium, magnesium, halogen atoms, and electron donors in the solid catalyst component (A), the content of titanium is from 0.5 to 8.0 wt %, preferably from 1.0 to 8.0 wt %, and still more preferably from 2.0 to 8.0 wt %; the content of magnesium is from 10 to 70 wt %, preferably from 10 to 50 wt %, more preferably from 15 to 40 wt %, and particularly preferably from 15 to 25 wt %; the content of halogen atoms is from 20 to 90 wt %, preferably from 30 to 85 wt %, more preferably from 40 to 80 wt %, and particularly preferably from 45 to 75 wt %; and the total amount of electron donor compounds is from 0.5 to 30 wt %, preferably from 1 to 25 wt %, and particularly preferably from 2 to 20 wt %.

Any compounds represented by the above formula (3) can be used without any specific limitations as the organoaluminum compound (B) (hereinafter referred to from time to time simply as "component (B)") for preparing the catalyst for the polymerization of olefins of the present invention. In the above formula (6), $R^6$ is preferably an ethyl group or an isobutyl group; Q is preferably a hydrogen atom, a chlorine atom, or a bromine atom; and p is preferably 2 or 3, and particularly preferably 3. As specific examples of such an organoaluminum compound (B), triethylaluminum, diethylaluminum chloride, triisobutylaluminum, diethylaluminum bromide, and diethylaluminum hydride can be given. These compounds may be used either individually or in combination of two or more. Triethylaluminum and triisobutylaluminum are preferably used.

The compounds represented by the above formula (2) can be given as the aminosilane compound (C) (hereinafter may be referred to from time to time as "component (C)") which can be used for preparing the catalyst for olefin polymerization of the present invention. Specific examples of the compounds shown by the formula (2) used as the component (C) are the same as those of the compounds shown by the formula (2) used for the catalyst component for olefin polymerization.

In addition to the above components, an organosilicon compound other than the above-described aminosilane compound (hereinafter may be simply referred to as "component (D)") may be used for preparing the catalyst for olefin polymerization of the present invention. As such an organosilicon compound (D), one or more organosilicon compounds shown by the formula $R^8_q Si(OR^9)_{4-q}$, wherein $R^8$ represents a hydrogen atom, an alkyl group, a cycloalkyl group, a phenyl group, a vinyl group, an allyl group, an aralkyl group, an alkylamino group, a cycloalkylamino group, or a polycyclic amino group having 1 to 20 carbon atoms, two or more $R^8$s which may be present being either the same or different, $R^9$ represents a linear or branched alkyl group, a cycloalkyl group, a vinyl group, an allyl group, or an aralkyl group having 1 to 20 carbon atoms, two or more $R^9$s which may be present being either the same or different, and q is an integer of 1 to 3.

As specific examples, alkylalkoxysilane, alkyl(cycloalkyl)alkoxysilane, cycloalkylalkoxysilane, phenylalkoxysilane, alkyl(phenyl)alkoxysilane, alkyl(alkylamino)alkoxysilane, alkylaminoalkoxysilane, cycloalkyl(alkylamino)alkoxysilane, alkyl(cycloalkylamino)alkoxysilane, polycyclic aminoalkoxysilane, and alkyl(polycyclic amino)alkoxysilane can be given.

As specific examples of the above-mentioned organosilicon compound (D) that can be preferably used, di-n-propyldimethoxysilane, diisopropyldimethoxysilane, di-n-butyldimethoxysilane, di-n-butyldiethoxysilane, t-butyl (methyl)dimethoxysilane, t-butyl(ethyl)dimethoxysilane, dicyclohexyldimethoxysilane, cyclohexyl(methyl)dimethoxysilane, dicyclopentyldimethoxysilane, cyclopentyl(methyl)diethoxysilane, cyclopentyl(ethyl)dimethoxysilane, cyclopentyl(cyclohexyl)dimethoxysilane, 3-methylcyclohexyl(cyclopentyl)dimethoxysilane, 4-methylcyclohexyl(cyclopentyl)dimethoxysilane, 3,5-dimethylcyclohexyl(cyclopentyl)dimethoxysilane, bis(diethylamino)dimethoxysilane, bis(di-n-propylamino)dimethoxysilane, bis(di-n-butylamino)dimethoxysilane, bis(di-t-butylamino)dimethoxysilane, bis(dicyclopentylamino)dimethoxysilane, bis(dicyclohexylamino)dimethoxysilane, bis(di-2-methylcyclohexylamino)dimethoxysilane, bis(perhydroisoquinolino)dimethoxysilane, bis(perhydroquinolino)dimethoxysilane, bis(ethyl-n-propylamino)dimethoxysilane, bis(ethylisopropylamino)dimethoxysilane, bis(ethyl-n-butylamino)dimethoxysilane, bis(ethylisobutylamino)dimethoxysilane, bis(ethyl-t-butylamino)dimethoxysilane, bis(isobutyl-n-propylamino)dimethoxysilane, bis(ethylcyclopentylamino)dimethoxysilane, bis(ethylcyclohexylamino)dimethoxysilane, ethyl(diethylamino)dimethoxysilane, n-propyl(diisopropylamino)dimethoxysilane, isopropyl(di-t-butylamino)dimethoxysilane, cyclohexyl(diethylamino)dimethoxysilane, ethyl(di-t-butylamino)dimethoxysilane, ethyl(perhydroisoquinolino)dimethoxysilane, n-propyl(perhydroisoquinolino)dimethoxysilane, isopropyl(perhydroisoquinolino)dimethoxysilane, n-butyl(perhydroisoquinolino)dimethoxysilane, ethyl(perhydroquinolino)dimethoxysilane, n-propyl(perhydroquinolino)dimethoxysilane, isopropyl(perhydroquinolino)dimethoxysilane, n-butyl(perhydroquinolino)dimethoxysilane, bis(diethylamino)diethoxysilane, bis(di-n-propylamino)diethoxysilane, bis(di-n-butylamino)diethoxysilane, bis(di-t-butylamino)diethoxysilane, bis(dicyclopentylamino)diethoxysilane, bis(dicyclohexylamino)diethoxysilane, bis(di-2-methylcyclohexylamino)diethoxysilane, bis(diperhydroisoquinolino)diethoxysilane, bis(perhydroquinolino)diethoxysilane, bis(ethyl-n-propylamino)diethoxysilane, bis(ethylisopropylamino)diethoxysilane, bis(ethyl-n-butylamino)diethoxysilane, bis(ethylisobutylamino)diethoxysilane, bis(ethyl-t-butylamino)diethoxysilane, bis(isobutyl-n-propylamino)diethoxysilane, bis(ethylcyclopentylamino)diethoxysilane, bis(ethylcyclohexylamino)diethoxysilane, n-propyl(diisopropylamino)diethoxysilane, ethyl(perhydroisoquinolino)diethoxysilane, n-propyl(perhydroisoquinolino)diethoxysilane, isopropyl(perhydroisoquinolino)diethoxysilane, n-butyl(perhydroisoquinolino)diethoxysilane, ethyl(perhydroquinolino)diethoxysilane, n-propyl(perhydroquinolino)diethoxysilane, isopropyl(perhydroquinolino)diethoxysilane, n-butyl(perhydroquinolino)diethoxysilane, thexyltrimethoxysilane, diethylaminotrimethoxysilane, di-n-propylaminotrimethoxysilane, di-n-butylaminotrimethoxysilane, di-t-butylaminotrimethoxysilane, dicyclopentylaminotrimethoxysilane, dicyclohexylaminotrimethoxysilane, di-2-methylcyclohexylaminotrimethoxysilane, perhydroisoquinolinotrimethoxysilane, perhydroquinolinotrimethoxysilane, diethylaminotriethoxysilane, di-n-propylaminotriethoxysilane, di-n-butylaminotriethoxysilane, ethyl-t-butylaminotriethoxysilane, ethyl-sec-butylaminotriethoxysilane, dicyclopentylaminotriethoxysilane, dicyclohexylaminotriethoxysilane, di-2-methylcyclohexylaminotriethoxysilane, perhydroisoquinolinotriethoxysilane, perhydroquinolinotriethoxysilane, bis(t-butylamino)dimethoxysilane, bis(cyclohexylamino)dimethoxysilane, bis(t-butylamino)diethoxysilane, bis(cyclohexylamino)diethoxysilane, trivinylmethylsilane, tetravinylsilane, and cyclohexylthexyldimethoxysilane can be given. Either one type of these organosilicon compounds (D) or a combination of two or more types of these compounds can be used in the present invention.

Olefins are polymerized or copolymerized by random or block copolymerization in the presence of the catalyst for olefin polymerization of the present invention. The olefins such as ethylene, propylene, 1-butene, 1-pentene, 4-methyl-1-pentene, and vinyl cyclohexane can be used either individually or in combination of two or more. Of these, ethylene, propylene, and 1-butene can be suitably used. A particularly preferable olefin is propylene. Propylene may be copolymerized with other olefins. As the olefins to be copolymerized, ethylene, 1-butene, 1-pentene, 4-methyl-1-pentene, vinyl cyclohexane, and the like can be used either individually or in combination of two or more. Of these, ethylene and 1-butene can be suitably used. As the method for copolymerizing propylene with other olefins, random copolymerization of polymerizing propylene as a copolymer with a small amount of ethylene in one step, and propylene-ethylene block copolymerization of polymerizing only propylene in a first step (first polymerization vessel) and copolymerizing propylene and ethylene in a second step (second polymerization vessel) are typical methods. The catalyst of the present invention comprising the component (A), component (B), and component (C) is effective in both the random copolymerization and block copolymerization for improving the catalytic activity, stereoregularity, and/or hydrogen response, copolymerization performance, and properties of resulting copolymers. In addition to the catalyst component (C), the above-described component (D) may be used. The components (C) and (D) may be used either as a mixture or separately in a multiple stage polymerization vessel of the block copolymerization. A known electron donor compound such as an alcohol, oxygen gas, or a ketone may be added to the polymerization reaction system in order to prevent formation of gel in the finished product, particularly when shifting from homopolymerization of propylene to the block copolymerization. As specific examples of the alcohol, ethyl alcohol and isopropyl alcohol can be given. These alcohols are used in an amount of 0.01 to 10 mol, and preferably 0.1 to 2 mol, for one mol of the component (B).

The ratio of each component used is not specifically limited inasmuch as such a ratio does not influence the effect of the present invention. Usually, the component (B) is used in an amount of 1 to 2000 mol, and preferably 50 to 1000 mol, per one mol of titanium atom in the component (A). The component (C) is used in an amount of 0.002 to 10 mol, preferably 0.01 to 2 mol, and particularly preferably 0.1 to 0.5 mol per one mol of the component (B). If the component (D) is used in combination, the amount is 0.002 to 10 mol, preferably 0.01 to 2 mol, and particularly preferably 0.01 to 0.5 mol, per one mol of the component (B), and the component (C) is used in the amount of 0.001 to 10 mol, preferably 0.01 to 10 mol, and particularly preferably 0.01 to 2 mol, per one mol of the component (C).

Although the order of contact of these components is optional, it is desirable to first add the organoaluminum compound (B) to the polymerization system, then cause the aminosilane compound (C) or a mixture of the components (C) and (D) to contact the organoaluminum compound (B), or cause the component (C) and component (D) in an optional order to contact the organoaluminum compound (B), and cause the solid catalyst component (A) to contact the resulting mixture. A method of forming a catalyst by adding the organoaluminum compound (B) to the polymerization system, separately causing the component (A) to contact the component (C) or the components (C) and (D), and feeding the contacted component (A) and component (C) or the components (C) and (D) to the polymerization system is also a preferable embodiment. It is possible to further improve the hydrogen response of the catalyst and crystalline properties of the resulting polymer by using a previously contacted mixture of the component (A) with the component (B) or the component (C), and the component (D).

In the present invention, polymerization can be carried out either in the presence or in the absence of an organic solvent. Olefin monomers such as propylene may be used either in a gaseous state or in a liquid state. The polymerization reaction is preferably carried out at a temperature of 200° C. or less, and preferably at 150° C. or less, under a pressure of 10 MPa or less, and preferably 6 MPa or less. Either a continuous polymerization system or a batch polymerization system may be used for the polymerization reaction. In addition, the polymerization can be completed either in one step or in two or more steps.

In polymerizing olefins using the catalyst formed from the component (A), component (B), and component (C) (hereinafter may be referred to from time to time as "main polymerization"), it is desirable to preliminarily polymerize the olefins prior to the main polymerization to further improve the catalyst activity, stereoregularity, properties of resulting polymer particles, and the like. In addition to the olefins used in the main polymerization, monomers such as styrene can be used in the preliminary polymerization. Specifically, after causing the component (A) to contact the component (B) and/or the component (C) in the presence of olefins to preliminarily polymerize 0.1 to 100 g of the polyolefins for 1 g of the component (A), the component (B) and/or the component (C) are further caused to contact to form the catalyst. In the case where the component (D) is used in combination, it is possible to cause the component (A) to contact the components (B) and (D) in the presence of olefins during the preliminary polymerization and to use the component (C) during the main polymerization. Although the order of contact of the components and monomers in carrying out the preliminary polymerization is optional, it is desirable to first add the component (B) to the preliminary polymerization system in an inert gas or olefin gas atmosphere such as propylene, cause the component (C) and/or the component (D) to come in contact with the component (A), and then cause an olefin such as propylene and/or one or more other olefins to come in contact with the mixture. Although not specifically limited, the preliminary polymerization temperature is from −10 to 70° C., and preferably from −5 to 50° C.

The polymerization of olefins in the presence of the olefin polymerization catalyst of the present invention can produce olefin polymers in a higher yield than in the polymerization using a known catalyst, while maintaining a higher stereoregularity of the polymer and improved hydrogen response. In addition, depending on the structure of the component (C), the catalytic activity and stereoregularity are improved as compared with the case in which a commonly-used catalyst is used. Specifically, when the catalyst of the present invention is used for polymerization of olefins, it has been confirmed that the hydrogen response is improved while maintaining high stereoregularity depending on the structure of the component (C). In addition, it has been confirmed that the effect of improving the catalytic activity and stereoregularity can be promoted by using of the component (C) having a specific structure. The organosilicon compound of the present invention can be used as a conductor insulation film material, a surface treating agent of a printed circuit board, a photoresist raw material or intermediate material thereof, and the like.

The present invention will be described in more detail by examples, which should not be construed as limiting the present invention.

Example 1

Synthesis of Aminosilane Compound

A flask in which the internal atmosphere was sufficiently replaced with nitrogen gas was charged with a THF solution of ethylamine in a nitrogen stream. The solution was cooled to −10 to 0° C. and a hexane solution of commercially available butyl lithium, in an amount equimolar to ethylamine, was slowly added using a dripping funnel while stirring. After the addition, the temperature was gradually increased to 50° C. and the mixture was reacted for two hours to obtain a slurry of lithium salt of ethylamine. Another flask in which the internal atmosphere was sufficiently replaced with nitrogen gas was charged with a toluene solution of dicyclopentyldimethoxysilane (a commercially available product) which was cooled to −10 to 0° C., and the above slurry of lithium salt of ethylamine, in an amount 2.1 times mol of the dicyclopentyldimethoxysilane, was slowly added using an injector in a nitrogen stream. After the addition, the temperature was gradually increased and the mixture was reacted at 70° C. for four hours. After the reaction, the reaction mixture was filtered in a nitrogen atmosphere and the solid components were washed with a small amount of toluene, thereby separating a solid from liquid. The solvent was evaporated from the solution and the main product of bis(ethylamino)dicyclopentylsilane was purified by distillation under reduced pressure. The boiling point of the compound was found to be 118° C./2.4 mmHg. The yield was 84.6%. This product was confirmed to be bis(ethylamino)dicyclopentylsilane by $^1$H-NMR, IR, and the elementary analysis. The elementary analysis confirmed that the compound consists of C: 66.05% (66.07%), H: 11.86% (11.86%), and N: 11.02% (11.01%), wherein the percentages of the parentheses are theoretical values. In addition, the IR spectrum had absorption by N—H stretching vibration typical to a secondary amine in the neighborhood of 3350 cm$^-$. The position attributable to protons obtained from the chart of $^1$H-NMR spectrum and the spectrum intensities of the positions are as shown in Table 1. The results of these analyses support that the compound obtained was bis(ethylamino)dicyclopentylsilane. $^1$H-NMR and IR were measured under the following conditions.

$^1$H-NMR: Measuring device: JEOL 500 MHZ, Solvent: CDCl$_3$, Number of scan: 20 times, Measuring temperature: 20° C., Internal standard: TMS IR: Measuring device: "Avatar 360FT/IR" manufactured by Nicolet Co, NaCl sandwiching method, Measurement temperature: room temperature

TABLE 1

| Type of proton | Number of protons | Peak position (ppm) |
|---|---|---|
| Proton of CH directly bonded to Si on 5-member ring | 2 | 0.8691 to 0.9411 (multiplet) |
| Proton CH$_2$ on 5-member ring | 16 | 1.0323 to 1.1203 (multiplet) |
| Proton of methyl group of ethylamino group | 6 | 1.3467 to 1.8118 (multiplet) |
| Proton of methylene group of ethylamino group | 4 | 2.7386 to 2.8870 (multiplet) |
| Proton of NH of ethylamino group | 2 | 04930 (broad singlet) |

Example 2

Synthesis of Aminosilane Compound

A three-necked flask in which the internal atmosphere was sufficiently replaced with nitrogen gas was charged with 60 ml of a THF solution containing 0.04 mol of ethylamine in a nitrogen stream. 30 ml of a hexane solution containing 0.04 mol of BuLi was slowly added to the ethylamine solution cooled to −10° C. using a dripping funnel. After the addition, the mixture was gradually heated and reacted at 50° C. for two hours. Another container of which the internal atmosphere was purged with nitrogen was charged with 60 ml of a toluene solution containing 0.02 mol of t-butylethyldimethoxysilane and cooled to −10° C. The above slurry of Li salt of methylamine was slowly added dropwise to the cooled solution under nitrogen seal. After the addition, the mixture was reacted at 50° C. for three hours. The reaction mixture was separated into a solid and a solution by centrifugation. The solid was washed with 20 ml of toluene and added to the solution. The solvent was evaporated from the solution under reduced pressure and the residue was distilled under reduced pressure to obtain bis(methylamino)-t-butylethylsilane. The elementary analysis confirmed that the compound consists of C: 55.01% (55.11%), H: 12.57% (12.72%), and N: 16.25% (16.07%), wherein the percentages of the parentheses are theoretical values.

Example 3

Synthesis of Aminosilane Compound

A flask in which the internal atmosphere was sufficiently replaced with nitrogen gas was charged with a THF solution of ethylamine. The solution was cooled to −10 to 0° C. and a hexane solution of commercially available butyl lithium, in an amount equimolar to ethylamine, was slowly added using a dripping funnel while stirring. After the addition, the temperature was gradually increased to 50° C. and the mixture was reacted for two hours to obtain a slurry of lithium salt of ethylamine. Another flask in which the internal atmosphere was sufficiently replaced with highly pure nitrogen gas was charged with a toluene solution of bis(methoxy)diisopropylsilane (a commercially available product) which was cooled to −10 to 0° C., and the above slurry of lithium salt of ethylamine, in an amount 2.1 times mol of the bis(methoxy)diisopropylsilane, was slowly added using an injector in a nitrogen stream. After the addition, the temperature was gradually increased and the mixture was reacted at 70° C. for four hours. After the reaction, the reaction mixture was filtered in a nitrogen atmosphere and the solid components were washed with a small amount of toluene, thereby separating a solid from liquid. The solvent was evaporated from the solution and the main product of bis(ethylamino)diisopropylsilane was purified by distillation under reduced pressure. The boiling point of the compound was found to be 68° C./7 mmHg. The yield was 87.2%. This product was confirmed to be bis(ethylamino)diisopropylsilane by $^1$H-NMR, IR, and the elementary analysis. The elementary analysis confirmed that the compound consists of C: 59.35% (59.34%), H: 12.96% (12.95%), and N: 13.82% (13.84%), wherein the percentages of the parentheses are theoretical values.

The IR spectrum had absorption by N—H stretching vibration typical to a secondary amine in the neighborhood of 3400 $cm^{-1}$. The position attributable to protons obtained from the chart of $^1$H-NMR spectrum and the spectrum intensities of the positions are as shown in Table 2. The results of these analyses support that the compound obtained was bis(ethylamino)diisopropylsilane. $^1$H-NMR and IR were measured under the same conditions as in Example 1.

TABLE 2

| Type of proton | Number of protons | Peak position (ppm) |
|---|---|---|
| Proton of CH directly bonded to Si on 5-member ring | 2 | 0.8102 to 0.8828 (multiplet) |
| Proton of methyl group of isopropyl group | 12 | 0.9861 to 0.9719 (multiplet) |
| Proton of methyl group of ethylamino group | 6 | 1.0477 to 1.1071 (multiplet) |
| Proton of methylene group of ethylamino group | 4 | 2.7924 to 2.8496 (multiplet) |
| Proton of NH of ethylamino group | 2 | 0.3903 (broad singlet) |

Example 4

Synthesis of Aminosilane Compound

The experiment was carried out in the same manner as in Example 2 except for using 0.02 mol of methylamine instead of 0.04 mol of methylamine, a hexane solution containing 0.02 mol of BuLi instead of the hexane solution containing 0.04 mol of BuLi, and 0.01 mol of t-butylethyldimethoxysilane instead of 0.02 mol of t-butylethyldimethoxysilane to obtain bis(methylamino)-t-butylmethylsilane. The elementary analysis confirmed that the compound consists of C: 52.30% (52.44%), H: 12.61% (12.57%), and N: 17.51% (17.47%), wherein the percentages of the parentheses are theoretical values.

Example 5

Synthesis of Aminosilane Compound

Bis(methylamino)dicyclohexylsilane was synthesized in the same manner as in Example 2, except that dicyclohexyldimethoxysilane was used instead of t-butylethyldimethoxysilane. The elementary analysis confirmed that the compound consists of C: 66.03% (66.07%), H: 11.86% (11.88%), and N: 11.00% (11.01%), wherein the percentages of the parentheses are theoretical values.

Example 6

Synthesis of Aminosilane Compound

Bis(methylamino)cyclohexylmethylsilane was synthesized in the same manner as in Example 2, except that cyclohexylmethyldimethoxysilane was used instead of t-butylethyldimethoxysilane. The elementary analysis confirmed that the compound consists of C: 57.91% (58.00%), H: 11.68% (11.90%), and N: 15.00% (15.03%), wherein the percentages of the parentheses are theoretical values.

Example 7

Synthesis of Aminosilane Compound

A flask purged with nitrogen was charged with 0.44 mol of metallic magnesium, and 60 ml of diisopropyl ether which was dehydrated and deoxidized was added. After further addition of a small amount of iodine as a catalyst, the mixture was stirred. The mixture was cooled to 10° C. while stirring and 140 ml of diisopropyl ether containing 0.4 mol of 2-chlorodecahydronaphthalene was slowly added dropwise, preferably while controlling the temperature at room temperature or below. After the addition, the mixture was reacted at 30° C. for two hours. The reaction mixture was filtered and the amount of the Grignard reagent in the resulting ether solution was calculated by acid-alkali titration. As a result, it was confirmed that the yield was 20% and the concentration was 0.04 mol/100 ml. A flask in which the internal atmosphere was sufficiently replaced with nitrogen gas was charged with 50 ml of a toluene solution containing 0.02 mol of tetramethoxysilane. The solution was cooled to −10° C. while stirring and 100 ml of a diisopropyl ether solution of the Grignard reagent having a decahydronaphthyl group, which was prepared above, was added dropwise. After the addition, the mixture was gradually heated and reacted at 80° C. for two hours. After the reaction, a solid component was separated by centrifugation in a nitrogen stream, washed twice with 10 ml of toluene, and added to the solution side. The solvent was evaporated under reduced pressure. The residue was heated and purified by distillation to separate a product. This procedure of synthesis was repeated twice. 50 ml of a toluene solution containing 0.02 mol of the resulting bis(decahydronaphthyl)dimethoxysilane was added to a flask.

On the other hand, a three-necked flask in which the internal atmosphere was sufficiently replaced with nitrogen gas was charged with 60 ml of a toluene solution containing 0.04 mol of ethylamine in a nitrogen stream. 30 ml of a hexane solution containing 0.04 mol of BuLi was slowly added to the ethylamine solution cooled to −10° C. using a dripping funnel. After the addition, the mixture was gradually heated and reacted at 50° C. for two hours, thereby obtaining a slurry of lithium salt of methylamine. The above toluene solution containing 0.02 mol of the bis(decahydronaphthyl)dimethoxysilane was cooled to −10° C. and the slurry of lithium salt of methylamine was added dropwise. After the addition, the mixture was further reacted for three hours at 50° C. and for two hours at 80° C. The solvent was evaporated under reduced pressure and the residue was distilled under reduced pressure to purify and separate the product, thereby obtaining bis(methylamino)bis(decahydronaphthyl)silane. The elementary analysis confirmed that the compound consists of C: 72.60% (72.86%), H: 11.61% (11.67%), and N: 7.51% (7.72%), wherein the percentages of the parentheses are theoretical values.

Example 8

Synthesis of Aminosilane Compound

Bis(ethylamino)cyclohexylcyclopentylsilane was synthesized in the same manner as in Example 2, except that ethylamine was used instead of methylamine and cyclohexylcyclopentyldimethoxysilane was used instead of t-butylethyldimethoxysilane. The elementary analysis confirmed that the compound consists of C: 67.05% (67.10%), H: 12.00% (12.01%), and N: 10.23% (10.43%), wherein the percentages of the parentheses are theoretical values.

Example 9

Preparation of Solid Catalyst Component

A 2,000 ml round bottom flask equipped with a stirrer, of which the internal atmosphere had been sufficiently replaced with nitrogen gas, was charged with 150 g of diethoxymagnesium and 750 ml of toluene to prepare a suspension liquid. The suspension liquid was added to a solution of 450 ml of toluene and 300 ml of titanium tetrachloride previously filled in another 2,000 ml round bottom flask equipped with a stirrer, of which the internal atmosphere had been sufficiently replaced with nitrogen gas. The suspension liquid was reacted at 5° C. for one hour. After the addition of 22.5 ml of di-n-butyl phthalate, the mixture was heated to 100° C. and reacted for two hours while stirring. After the reaction, the resulting reaction mixture was washed four times with 1,300 ml of toluene at 80° C. After the addition of 1,200 ml of toluene and 300 ml of titanium tetrachloride, the reaction mixture was heated to 110° C. and reacted for two hours while stirring. The intermediate washing and the secondary treatment were repeated once more. The resulting reaction mixture was washed seven times with 1,300 ml of heptane at 40° C., filtered, and dried to obtain a solid catalyst component in the form of a powder. The content of titanium in the solid component was measured and found to be 3.1 wt %.

<Preparation of Polymerization Catalyst and Polymerization>

A 2.0 l autoclave equipped with a stirrer, of which the internal atmosphere had been entirely replaced with nitrogen gas, was charged with 1.32 mmol of triethylaluminum, 0.26 mmol of bis(ethylamino)dicyclopentylsilane obtained in Example 1, and the above solid catalyst component in an amount, in terms of the titanium atom contained therein, of 0.0026 mmol, thereby forming a polymerization catalyst. Then, with the addition of 4 l of hydrogen gas and 1.4 l of liquefied propylene, preliminary polymerization was carried out for five minutes at 20° C., following which the preliminary polymerization product was heated and polymerization was carried out for one hour at 70° C. The catalyst activity, bulk density (BD, g/ml), heptane insoluble components (HI, wt %), and melt flow rate according to ASTM, in terms of the melt index (MI, g-PP/10 min), of the resulting polymer were measured. The results are shown in Table 4. Blanks in the Table 4 indicate that no data was acquired.

The catalytic activity per gram of the solid catalyst component for the amount of polymer (F) gram per one hour of the polymerization time was calculated according to the following formula:

Catalytic activity=Produced polymer $(F)(g)$/Solid catalyst component $(g)$/hour The polymer (H)(g) insoluble in n-heptane after continuously extracting this polymer (G) for six hours in boiling n-heptane was dried and the weight was measured to determine the proportion of the components insoluble in boiling n-heptane (HI, wt %) in this polymer according to the following formula:

HI (wt %)=$(H)(g)/(G)(g)\times 100$

The melt index (MI) which indicates the melt flow rate of the polymer was determined according to the method conforming to ASTEM D1238 or JIS K7210.

The molecular weight distribution of polymers was evaluated by the ratio (Mw/Mn) of the weight average molecular weight (Mw) to the number average molecular weight (Mn) measured by cross fractionation chromatography (CFC) using "CFC T-150B" (manufactured by Mitsubishi Chemical Corp.) under the following conditions.
Solvent: o-dichlorobenzene (ODCB)
Temperature: 140° C. (SEC)
Column: Shodex GPC UT-806 m$^2$
Sample concentration: 4 g/l-ODCB (200 mg/50 ml-ODCB)
Feed amount: 0.5 ml
Flow rate: 1.0 ml/min
Temperature range: 0 to 140° C.

Example 10

The same experiment as in Example 9 was carried out, except for using bis(methylamino)-t-butylethylsilane obtained in Example 2 instead of bis(ethylamino)dicyclopentylsilane. The results are shown in Table 4.

Example 11

The same experiment as in Example 9 was carried out, except for using bis(ethylamino)diisopropylsilane obtained in Example 3 instead of bis(ethylamino)dicyclopentylsilane. The results are shown in Table 4.

Example 12

The same experiment as in Example 9 was carried out, except for using bis(methylamino)-t-butylmethylsilane obtained in Example 4 instead of bis(ethylamino)dicyclopentylsilane. The results are shown in Table 4.

Example 13

The same experiment as in Example 9 was carried out, except for using bis(methylamino)dicyclohexylsilane obtained in Example 5 instead of bis(ethylamino)dicyclopentylsilane. The molecular weight distribution of the polymer was measured. The results are shown in Table 4.

Example 14

The same experiment as in Example 9 was carried out, except for using bis(methylamino)cyclohexylmethylsilane obtained in Example 6 instead of bis(ethylamino)dicyclopentylsilane. The results are shown in Table 4.

Example 15

The same experiment as in Example 9 was carried out, except for using bis(methylamino)bis(decahydronaphthyl)silane obtained in Example 7 instead of bis(ethylamino)dicyclopentylsilane. The results are shown in Table 4.

Example 16

The same experiment as in Example 9 was carried out, except for using bis(ethylamino)cyclohexylcyclopentylsilane obtained in Example 8 instead of bis(ethylamino)dicyclopentylsilane. The results are shown in Table 4.

Example 17

Preparation of Solid Catalyst Component

A 500 ml round bottom flask equipped with a stirrer, of which the internal atmosphere had been sufficiently replaced with nitrogen gas, was charged with 4.76 g of anhydrous magnesium chloride, 25 ml of decane, and 23.4 ml of 2-ethylhexyl alcohol. The mixture was reacted for two hours at 130° C. to obtain a homogeneous solution. Then, 1.11 g of phthalic anhydride was added to the homogeneous solution and the mixture was reacted at 130° C. for one hour. All the resulting reaction solution was added dropwise over one hour to 200 ml of titanium tetrachloride maintained at −20° C. in another 500 ml round bottom flask equipped with a stirrer, of which the internal atmosphere had been sufficiently replaced with nitrogen gas. The mixed solution was heated to 110° C. for four hours and 2.68 ml of diisobutyl phthalate was added. The mixture was reacted for two hours. After the reaction, the liquid portion was removed by filtration. The remaining solid was washed with decane and hexane at 110° C. until no free titanium compounds were detected, filtered, and dried to obtain a solid catalyst component in the form of a powder. The content of titanium in the solid catalyst component was measured and found to be 3.1 wt %.

<Preparation of Polymerization Catalyst and Polymerization>

A polymerization catalyst was prepared and polymerization was carried out in the same manner as in Example 9, except for using the solid catalyst component prepared above. The results are shown in Table 4.

Example 18

Preparation of Solid Catalyst Component

A 1,000 ml round bottom flask equipped with a stirrer, of which the internal atmosphere had been sufficiently replaced with nitrogen gas, was charged with 32 g of magnesium flake used as a Grignard agent. A mixture of 120 g of butyl chloride and 500 ml of dibutyl ether was added dropwise to the magnesium over four hours at 50° C., and then the mixture was reacted for one hour at 60° C. After the reaction, the reaction solution was cooled to room temperature and the solid components were removed by filtration to obtain a solution of the magnesium compound. 150 ml of the magnesium compound solution was added dropwise over four hours at 5° C. to a homogeneous solution which was prepared from 240 ml of hexane, 5.4 g of tetrabutoxytitanium, and 61.4 g of tetraethoxysilane in a 500 ml round bottom flask equipped with a stirrer, of which the internal atmosphere had been sufficiently replaced with nitrogen gas. After the reaction, the mixture was stirred for one hour at room temperature. The resulting reaction solution was filtered at room temperature to remove a liquid portion. The resulting solid was washed eight times with 240 ml of hexane, and dried under reduced pressure to obtain a solid product. 8.6 g of the solid product was added to a 100 ml round bottom flask equipped with a stirrer, of which the internal atmosphere had been sufficiently replaced with nitrogen gas, followed by the addition of 48 ml of toluene and 5.8 ml of diisobutyl phthalate. The mixture was reacted for one hour at 95° C. Next, the liquid portion was removed by filtration and the solid residue was washed eight times with 85 ml of toluene. After washing, 21 ml of toluene, 0.48 ml of diisobutyl phthalate, and 12.8 ml of titanium tetrachloride were added to the flask. Then, the mixture was reacted at 95° C. for eight hours. After the reaction, the solid was separated from the liquid at 95° C., washed twice with 48 ml of toluene, and again treated with a mixture of diisobutyl phthalate and titanium tetrachloride under the same conditions as above. The resulting solid was washed eight times with 48 ml of hexane, filtered, and dried to obtain a solid catalyst component in the form of a powder. The content of titanium in the solid catalyst component was analyzed and found to be 2.1 wt %.

<Preparation of Polymerization Catalyst and Polymerization>

A polymerization catalyst was prepared and polymerization was carried out in the same manner as in Example 9, except for using the solid catalyst component prepared above. The results are shown in Table 4.

Example 19

The same experiment as in Example 9 was carried out except for extending the reaction time from one hour to two hours. The results are shown in Table 4.

Example 20

A solid catalyst component was prepared, a polymerization catalyst was prepared, and polymerization was carried out in the same manner as in Example 9, except that tris(methylamino)-t-butylsilane was used instead of bis(ethylamino)dicyclopentylsilane. The results are shown in Table 5.

Example 21

A solid catalyst component was prepared, a polymerization catalyst was prepared, and polymerization was carried out in the same manner as in Example 9, except that bis(methylamino)-di-t-butylsilane was used instead of bis(ethylamino)dicyclopentylsilane. The results are shown in Table 5.

Example 22

A solid catalyst component was prepared, a polymerization catalyst was prepared, and polymerization was carried out in the same manner as in Example 9, except that bis(methylamino)cyclohexylcyclopentylsilane was used instead of bis(ethylamino)dicyclopentylsilane. The results are shown in Table 5.

Example 23

A solid catalyst component was prepared, a polymerization catalyst was prepared, and polymerization was carried out in the same manner as in Example 9, except that bis(methylamino)cyclohexylthexylsilane was used instead of bis(ethylamino)dicyclopentylsilane. The results are shown in Table 5.

Example 24

A solid catalyst component was prepared, a polymerization catalyst was prepared, and polymerization was carried out in the same manner as in Example 9, except that bis(ethylamino)-t-butylisobutylsilane was used instead of bis(ethylamino)dicyclopentylsilane. The results are shown in Table 5.

Example 25

A solid catalyst component was prepared, a polymerization catalyst was prepared, and polymerization was carried out in the same manner as in Example 9, except that bis(methylamino)-di-4-methoxyphenylsilane was used instead of bis(ethylamino)dicyclopentylsilane. The results are shown in Table 5.

Example 26

A solid catalyst component was prepared, a polymerization catalyst was prepared, and polymerization was carried out in the same manner as in Example 9, except that bis(methylamino)thexylmethylsilane was used instead of bis(ethylamino)dicyclopentylsilane. The results are shown in Table 5.

Example 27

A solid catalyst component was prepared, a polymerization catalyst was prepared, and polymerization was carried out in the same manner as in Example 9, except that bis(methylamino)didecahydronaphthylsilane was used instead of bis(ethylamino)dicyclopentylsilane. The results are shown in Table 5.

Example 28

A solid catalyst component was prepared, a polymerization catalyst was prepared, and polymerization was carried out in the same manner as in Example 9, except that tris(methylamino)cyclohexylsilane was used instead of bis(ethylamino)dicyclopentylsilane. The results are shown in Table 5.

Comparative Example 1

A solid catalyst component was prepared, a polymerization catalyst was prepared, and polymerization was carried out in the same manner as in Example 9, except that cyclohexylmethyldimethoxysilane was used instead of bis(ethylamino)dicyclopentylsilane. The results are shown in Table 4.

Comparative Example 2

A solid catalyst component was prepared, a polymerization catalyst was prepared, and polymerization was carried out in the same manner as in Example 9, except that bis(diethylamino)dimethoxysilane was used instead of bis(ethylamino)dicyclopentylsilane. The results are shown in Table 4.

Comparative Example 3

A solid catalyst component was prepared, a polymerization catalyst was prepared, and polymerization was carried out in the same manner as in Example 9, except that diisopropylaminotriethoxysilane was used instead of bis(ethylamino)dicyclopentylsilane. The results are shown in Table 4.

Comparative Example 4

A solid catalyst component was prepared, a polymerization catalyst was prepared, and polymerization was carried out in the same manner as in Example 9, except that tris(dimethylamino)methoxysilane was used instead of bis(ethylamino)dicyclopentylsilane. The results are shown in Table 4.

Comparative Example 5

A solid catalyst component was prepared, a polymerization catalyst was prepared, and polymerization was carried out in the same manner as in Example 9, except that cyclohexylmethyldimethoxysilane was used instead of bis(ethylamino)dicyclopentylsilane and the polymerization time was extended from one hour to two hours. The results are shown in Table 4.

Example 29

Synthesis of Aminosilane Compound

Bis(methylamino)dicyclopentylsilane was synthesized in the same manner as in Example 1, except that methylamine was used instead of ethylamine. The yield was 82.5%. This product was confirmed to be bis(methylamino)dicyclopentylsilane by the elementary analysis. The elementary analysis confirmed that the compound consists of C: 63.53% (63.65%), H: 11.56% (11.57%), and N: 12.35% (12.37%) wherein the percentages of the parentheses are theoretical values.

Example 30

Synthesis of Aminosilane Compound

Bis(n-propylamino)dicyclopentylsilane was synthesized in the same manner as in Example 1, except that n-propylamine was used instead of ethylamine. The yield was 82.5%. This product was confirmed to be bis(n-propylamino)dicyclopentylsilane by the elementary analysis. The elementary analysis confirmed that the compound consists of C: 68.03% (68.02%), H: 12.15% (12.13%), and N: 9.90% (9.91%) wherein the percentages of the parentheses are theoretical values.

Example 31

Preparation of Polymerization Catalyst and Polymerization

A solid catalyst component was prepared, a polymerization catalyst was prepared, and polymerization was carried out in the same manner as in Example 9, except that bis(methylamino)dicyclopentylsilane prepared in Example 29 was used instead of bis(ethylamino)dicyclopentylsilane. The results are shown in Table 4.

Example 32

Preparation of Polymerization Catalyst and Polymerization

A solid catalyst component was prepared, a polymerization catalyst was prepared, and polymerization was carried out in the same manner as in Example 9, except that bis(n-propylamino)dicyclopentylsilane prepared in Example 30 was used instead of bis(ethylamino)dicyclopentylsilane. The results are shown in Table 4.

Example 33

Synthesis of Aminosilane Compound

A three-necked flask equipped with a stirrer, of which the internal atmosphere was sufficiently replaced with dried nitrogen gas, was charged with a dehydrated/deoxidized toluene solution (toluene: 100 ml) containing 0.9 mol of dehydrated/deoxidized methylamine in a nitrogen stream and cooled to −10° C. Then, a solution of toluene (50 ml) containing 0.2 mol of silicon tetrachloride was slowly added dropwise from a dripping funnel for 30 minutes, while stirring the mixture. The reaction was exothermic and a white precipitate which contains hydrochloride of amine was produced simultaneously with dripping. After the addition, the mixture was allowed to cool to room temperature. Then, the mixture was heated to 40° C. and reacted for one hour. After the reaction, the reaction mixture was filtered in a nitrogen gas atmosphere and the solid components were washed with 10 ml of toluene, thereby separating a solid from liquid.

The resulting toluene solution was concentrated under reduced pressure at 50° C. to a volume of one fourth of the original volume, and 150 ml of dehydrated/deoxidized n-heptane was added. The mixture was cooled to 10° C. and allowed to stand overnight to recrystallize a solid. The precipitated needle-like crystals were collected by filtration and dried under nitrogen gas atmosphere to obtain tetrakis(m-ethylamino)silane. Based on the weight of crystals, the yield of first recrystallization was confirmed to be 50%. The residue was subjected to second recrystallization and the resulting crystals were added. The yield became 55%. As a result of elementary analysis, the compound was found to consist of C: 32.23% (32.40%), H: 10.67% (10.88%), and N: 37.70% (37.78%), wherein the percentages of the parentheses are theoretical values.

Example 34

Synthesis of Aminosilane Compound

A flask of which the internal atmosphere was sufficiently purged with nitrogen gas was charged with 50 ml of a toluene solution containing 0.2 mol of t-butylamine and cooled to −10° C. while stirring. 60 ml of a THF solution containing 0.2 mol of BuMgCl was slowly added to the cooled solution using a dripping funnel. After the addition, the mixture was gradually heated and reacted at 40° C. for two hours to complete the reaction. Next, a flask of which the internal atmosphere was sufficiently purged with nitrogen gas was charged with 50 ml of a toluene solution containing 0.1 mol of tetramethoxysilane and cooled to −10° C. while stirring. A slurry of Mg salt of t-butylamine obtained by the above reaction was slowly added using a dripping funnel. After the addition, the mixture was gradually heated and reacted at 50° C. for three hours. The produced solid was separated from liquid by centrifugation in a nitrogen stream. The solid was washed twice with 20 ml of toluene and added to the solution. The solvent was evaporated under reduced pressure. The residue was distilled under reduced pressure to purify bis(t-butylamino)dimethoxysilane which is the main product.

A flask of which the internal atmosphere was sufficiently purged with nitrogen gas was charged with 50 ml of a toluene solution containing 0.1 mol of ethylamine and cooled to −10° C. while stirring. 60 ml of a THF solution containing 0.1 mol of BuMgCl was slowly added to the cooled solution using a dripping funnel. After the addition, the mixture was gradually heated and reacted at 20° C. for two hours to complete the reaction. Next, a flask of which the internal atmosphere was sufficiently purged with nitrogen gas was charged with 50 ml of a toluene solution containing 0.05 mol of bis(t-butylamino)dimethoxysilane and cooled to −10° C. while stirring. A slurry of a mixture of Mg salt of ethylamine obtained by the above reaction was slowly added using a dripping funnel to the toluene solution containing bis(t-butylamino)dimethoxysilane. After the addition, the mixture was reacted at 50° C. for four hours. The produced solid was separated by centrifugation in a nitrogen stream. The solid was washed twice with 20 ml of toluene and added to the solution. The solvent was evaporated under reduced pressure. The residue was distilled under reduced pressure to purify bis(t-butylamino)bis(diethylamino)silane which is the main product. As a result of elementary analysis, the compound was found to consist of C: 55.30% (55.33%), H: 12.32% (12.38%), and N: 21.39% (21.51%), wherein the percentages of the parentheses are theoretical values.

Example 35

Synthesis of Aminosilane Compound

Bis(perhydroquinolino)dimethoxysilane was synthesized by a general synthesis method. Next, 110 ml of a reaction mixture containing 0.1 mol of Mg salt of diethylamine was produced according to the method of Example 34. A flask of which the internal atmosphere was sufficiently purged with nitrogen gas was charged with 80 ml of a toluene solution containing 0.05 mol of bis(perhydroquinolino)dimethoxysilane and cooled to −10° C. while stirring. Next, 110 ml of the slurry-like reaction mixture containing 0.1 mol of Mg salt of diethylamine was slowly added to the above solution using a dripping funnel. After the addition, the mixture was reacted at 60° C. for six hours. The produced solid was separated by centrifugation in a nitrogen stream. The solid was washed twice with 20 ml of toluene and added to the solution. The solvent was evaporated under reduced pressure. The residue was distilled under reduced pressure to purify bis(perhydroquinolino)bis(ethylamino)silane which is the main product. As a result of elementary analysis, the compound was found to consist of C: 67.20% (67.29%), H: 11.30% (11.29%), and N: 14.25% (14.27%), wherein the percentages of the parentheses are theoretical values.

Example 36

Synthesis of Aminosilane Compound

A three-necked flask of which the internal atmosphere was sufficiently purged with nitrogen gas was charged with 80 ml of a toluene solution containing 0.05 mol of di-t-butylamine in a nitrogen stream and cooled to −10° C. while stirring. 50 ml of a THF solution containing 0.05 mol of BuMgCl was slowly added to the above toluene solution containing di-t-butylamine using a dripping funnel. After the addition, the mixture was heated to 40° C. and reacted for two hours, thereby obtaining a slurry of Mg salt of di-t-butylamine. Next, a three-necked flask of which the internal atmosphere was sufficiently purged with nitrogen gas was charged with 50 ml of a toluene solution containing 0.05 mol of tetramethoxysilane in a nitrogen stream and cooled to −10° C. while stirring. All the amount of the above-mentioned slurry of Mg salt of di-t-butylamine was slowly added using a dripping funnel to the toluene solution containing tetramethoxysilane. After the addition, the mixture was heated to 50° C. and reacted at the same temperature for four hours. The solvent was evaporated from the solution under reduced pressure and the main product of (di-t-butylamino)trimethoxysilane was purified by distillation under reduced pressure. A three-necked flask of which the internal atmosphere was sufficiently purged with nitrogen gas was charged with the toluene solution containing 0.03 mol of (di-t-butylamino)trimethoxysilane in a nitrogen stream and cooled to −10° C. while stirring. In the same manner as in Example 35, a slurry containing 0.09 mol of Mg salt of diethylamine synthesized from diethylamine and BuMgCl was slowly added to the above toluene solution containing 0.03 mol of (di-t-butylamino)trimethoxysilane using a dripping funnel. After the addition, the mixture was gradually heated and reacted at 50° C. for four hours. After the reaction, the solid was separated from the solution by centrifugation in a nitrogen stream, washed twice with 20 ml of toluene, and added to the solution. The solvent was evaporated from the solution under reduced pressure and the main product of tris(ethylamino)di-t-butylaminosilane was purified by distillation under reduced pressure. As a result of elementary analysis, the compound was found to consist of C: 58.30% (58.27%), H: 12.41% (12.58%), and N: 19.25% (19.42%), wherein the percentages of the parentheses are theoretical values.

Example 37

Synthesis of Aminosilane Compound

A slurry of 0.1 mol of Mg salt of di-t-butylamine was prepared in the same synthesis method of Example 36. Next, a three-necked flask of which the internal atmosphere was sufficiently purged with nitrogen gas was charged with 50 ml of a toluene solution containing 0.05 mol of tetramethoxysilane in a nitrogen stream and cooled to −10° C. while stirring. 100 ml of the above-mentioned slurry of 0.1 mol of Mg salt of di-t-butylamine was slowly added using a dripping funnel to the toluene solution. After the addition, the mixture was reacted at 60° C. for four hours. After the reaction, the solid was separated from the solution by centrifugation in a nitrogen stream, washed with 20 ml of toluene, and added to the solution. The solvent was evaporated from the solution under reduced pressure and the main product of bis(di-t-butylamino)dimethoxysilane was purified by distillation under reduced pressure. A slurry (80 ml) of 0.08 mol of Mg salt of methylamine was synthesized by the reaction of methylamine and BuMgCl from in the same manner as in Example 36. A three-necked flask of which the internal atmosphere was sufficiently purged with nitrogen gas was charged with a toluene solution containing 0.04 mol of bis(di-t-butylamino)dimethoxysilane in a nitrogen stream and cooled to −10° C. while stirring. 80 ml of the above-mentioned slurry of 0.08 mol Mg salt of methylamine was slowly added using a dripping funnel to this solution. After the addition, the mixture was gradually heated and reacted at 70° C. for five hours. After the reaction, a solid was separated by centrifugation in a nitrogen stream. The solid was washed twice with 20 mol of toluene and added to the solution. The solvent was evaporated under reduced pressure and the main product of bis(di-t-butylamino)bis(methylamino)silane was purified by distillation under reduced pressure. As a result of elementary analysis, the compound was found to consist of C: 62.48% (62.73%), H: 12.41% (12.87%), and N: 16.20% (16.26%), wherein the percentages of the parentheses are theoretical values.

Example 38

Synthesis of Aminosilane Compound

A three-necked flask in which the internal atmosphere was sufficiently replaced with nitrogen gas was charged with 50 ml of a THF solution containing 0.05 mol of ethylamine. The solution was cooled to −10° C. and 5 ml of a hexane solution of BuLi, in an amount equimolar to ethylamine (0.01 mol/ml solution), was added dropwise to obtain Li salt of ethylamine. A heptane solution containing 0.025 mmol of bis(perhydroisoquinolino)dimethoxysilane which was cooled to −10° C. was added dropwise to the reaction mixture. After the addition, the mixture was gradually heated and reacted at 50° C. for two hours. After the reaction, the produced solid was separated from liquid by centrifugation in a nitrogen stream. The solid was washed twice with heptane. The washing liquid was added and the solution was concentrated under reduced pressure. The concentrate was analyzed by gas chromatography to observe, in addition to three peaks due to the residual solvent and cis, trans structural isomers of bis(perhydroisoquinolino), a peak which is presumed to be due to a very small amount (1 to 2%) of mono-substituted derivative. As a result of purification by distillation under reduced pressure, bis (ethylamino)bis(perhydroisoquinolino)silane was obtained. The elementary analysis of the resulting compound confirmed that the compound consists of C: 67.41% (67.29%), H: 11.10% (11.29%), and N: 14.11% (14.27%), wherein the percentages of the parentheses are theoretical values.

Example 39

Synthesis of Aminosilane Compound

A three-necked flask in which the internal atmosphere was sufficiently replaced with nitrogen gas was charged with 50 ml of a THF solution of diethylamine (0.1 mol/50 ml). The solution was cooled to −10° C. while stirring and 100 ml of a THF solution of BuMgCl (0.1 mol/100 ml) was slowly added dropwise using a dripping funnel. After the addition, the mixture was reacted at 40° C. for two hours to complete the reaction. A slurry of Mg salt of diethylamine obtained in this manner was slowly added to 50 ml of a 0.09 mol/50 ml toluene solution of tetrakis(ethylamino)silane synthesized according to the method of Example 33 at −10° C. while stirring. After the addition, the mixture was allowed to react at 50° C. for two hours. The reaction product was centrifuged in a nitrogen stream to separate a solid from liquid. The solid was washed twice with toluene. The solution was concentrated and purified by distillation under reduced pressure. Tris(ethylamino)(diethylamino)silane thus obtained was subjected to elementary analysis to confirm that the compound consists of C: 41.32% (51.67%), H: 12.10% (12.14%), and N: 23.98% (24.10%), wherein the percentages of the parentheses are theoretical values.

Example 40

Synthesis of Aminosilane Compound

A three-necked flask in which the internal atmosphere was sufficiently replaced with nitrogen gas was charged with 100 ml of a THF solution of diethylamine (0.1 mol/50 ml). The solution was cooled to −10° C. and 200 ml of a THF solution of BuMgCl (0.1 mol/100 ml) was slowly added dropwise using a dripping funnel. After the addition, the mixture was reacted at 40° C. for two hours to complete the reaction. A slurry of Mg salt of diethylamine obtained in this manner was slowly added to 50 ml of a 0.09 mol/50 ml toluene solution of tetrakis(ethylamino)silane synthesized according to the method of Example 33 at −10° C. while stirring. After the addition, the mixture was reacted at 60° C. for three hours. The reaction product was centrifuged in a nitrogen stream to separate a solid from liquid. The solid was washed twice with toluene. The solution was concentrated and purified by distillation under reduced pressure. Bis(ethylamino)bis(diethylamino)silane thus obtained was subjected to elementary analysis to confirm that the compound consists of C: 55.23% (55.33%), H: 12.30% (12.38%), and N: 21.49% (21.51%), wherein the percentages of the parentheses are theoretical values.

Example 41

Synthesis of Aminosilane Compound

A three-necked flask in which the internal atmosphere was sufficiently replaced with nitrogen gas was charged with 50 ml of a THF solution of t-butylethylamine (0.05 mol/50 ml). The solution was cooled to −10° C. while stirring and 50 ml of a THF solution of BuMgCl (0.05 mol/50 ml) was slowly added dropwise using a dripping funnel. After the addition, the mixture was reacted at 40° C. for two hours. A slurry of Mg salt of t-butylethylamine obtained in this manner was added dropwise to a flask cooled to −10° C., which contained 50 ml of a 0.05 mol/50 ml toluene solution of tetrakis(methylamino)silane synthesized in the same manner as in Example 33. After the addition, the mixture was reacted at 50° C. for two hours. The resulting reaction mixture was concentrated to about one half of the original volume under reduced pressure at room temperature, and the solid was separated from liquid by centrifugation in a nitrogen stream. The solid was washed twice with 15 ml of toluene. The solvent was evaporated from the solution under reduced pressure and the resulting product was purified by distillation under reduced pressure. The yield was 50%, which was equivalent to the theoretical value. Tris(methylamino)(t-butylethylamino)silane thus obtained was subjected to elementary analysis to confirm that the compound consists of C: 49.41% (49.49%), H: 12.01% (12.00%), and N: 25.61% (25.65%), wherein the percentages of the parentheses are theoretical values.

Example 42

Synthesis of Aminosilane Compound

A three-necked flask of which the internal atmosphere was sufficiently purged with nitrogen gas was charged with 80 ml of a toluene solution containing 0.05 mol of diisopropylamine in a nitrogen stream and cooled to −10° C. while stirring. 50 ml of a THF solution containing 0.05 mol of BuMgCl was slowly added to the above toluene solution containing diisopropylamine using a dripping funnel. After the addition, the mixture was heated to 50° C. and reacted for two hours, thereby obtaining a slurry of Mg salt of diisopropylamine. Next, a three-necked flask of which the internal atmosphere was sufficiently purged with nitrogen gas was charged with 50 ml of a toluene solution containing 0.05 mol of tetramethoxysilane in a nitrogen stream and cooled to −10° C. while stirring. All the amount of the above-mentioned slurry of Mg salt of diisopropylamine was slowly added using a dripping funnel to the toluene solution containing tetramethoxysilane. After the addition, the mixture was heated to 50° C. and reacted at that temperature for three hours. The solvent was evaporated from the solution under reduced pressure and the main product of (diisopropylamino)trimethoxysilane was purified by distillation under reduced pressure. A slurry containing Mg salt of methylamine was prepared by the reaction of 0.09 mol of BuMgCl and an equimolar amount of methylamine according to the method of Example 36. A three-necked flask of which the internal atmosphere was sufficiently purged with nitrogen gas was charged with the toluene solution containing 0.03 mol of (diisopropylamino)trimethoxysilane in a nitrogen stream and cooled to −10° C. while stirring. A slurry containing 0.09 mol of Mg salt of methylamine was slowly added dropwise using a dripping funnel to this solution. After the addition, the mixture was gradually heated and reacted at 60° C. for five hours. After the reaction, a solid was separated by centrifugation in a nitrogen stream. The solid was washed twice with 20 mol of toluene and added to the solution. The solvent was evaporated from the solution under reduced pressure and the main product of tris(methylamino)diisopropylaminosilane was purified by distillation under reduced pressure. As a result of elementary analysis, the compound was found to consist of C: 49.42% (49.49%), H: 12.11% (12.00%), and N: 25.45% (25.65%), wherein the percentages of the parentheses are theoretical values.

Example 43

The same experiment as in Example 9 was carried out, except for using tetrakis(methylamino)silane obtained in Example 33 instead of bis(ethylamino)dicyclopentylsilane. The results are shown in Table 6.

Example 44

The experiment was carried out in the same manner as in Example 43, except that the amount of hydrogen gas used for preparing the polymerization catalyst and carrying out the polymerization reaction was decreased to 1 l from 4 l. The results are shown in Table 6.

Example 45

The same experiment as in Example 9 was carried out, except for using 0.13 mmol of bis(t-butylamino)bis(diethylamino)silane obtained in Example 34 instead of 0.26 mmol of bis(ethylamino)dicyclopentylsilane. The results are shown in Table 6.

Example 46

The same experiment as in Example 9 was carried out, except for using 0.13 mmol of bis(perhydroquinolino)bis(diethylamino)silane obtained in Example 35 instead of 0.26 mmol of bis(ethylamino)dicyclopentylsilane. The results are shown in Table 6.

Example 47

The same experiment as in Example 9 was carried out, except for using 0.13 mmol of tris(ethylamino)di-t-butylaminosilane obtained in Example 36 instead of 0.26 mmol of bis(ethylamino)dicyclopentylsilane. The results are shown in Table 6.

Example 48

The same experiment as in Example 9 was carried out, except for using 0.13 mmol of bis(di-t-butylamino)bis(methylamino)silane obtained in Example 37 instead of 0.26 mmol of bis(ethylamino)dicyclopentylsilane. The results are shown in Table 6.

Example 49

The same experiment as in Example 9 was carried out, except for using 0.13 mmol of bis(ethylamino)bis(perhydroisoquinolino)silane obtained in Example 38 instead of 0.26 mmol of bis(ethylamino)dicyclopentylsilane. The results are shown in Table 6.

Example 50

The same experiment as in Example 9 was carried out, except for using 0.13 mmol of tris(ethylamino)bis(diethylamino)silane obtained in Example 39 instead of 0.26 mmol of bis(ethylamino)dicyclopentylsilane. The results are shown in Table 6.

Example 51

The same experiment as in Example 9 was carried out, except for using 0.13 mmol of bis(ethylamino)bis(diethylamino)silane obtained in Example 40 instead of 0.26 mmol of bis(ethylamino)dicyclopentylsilane. The results are shown in Table 6.

Example 52

The same experiment as in Example 9 was carried out, except for using tris(methylamino)(t-butylethylamino)silane obtained in Example 41 instead of bis(ethylamino)dicyclopentylsilane. The results are shown in Table 6.

Example 53

The same experiment as in Example 9 was carried out, except for using tris(methylamino)diisopropylaminosilane obtained in Example 42 instead of bis(ethylamino)dicyclopentylsilane. The results are shown in Table 6.

Example 54

The same experiment as in Example 17 was carried out, except for using tetrakis(methylamino)silane obtained in Example 33 instead of bis(ethylamino)dicyclopentylsilane. The results are shown in Table 6.

Example 55

The same experiment as in Example 18 was carried out, except for using tetrakis(methylamino)silane obtained in Example 33 instead of bis(ethylamino)dicyclopentylsilane. The results are shown in Table 6.

Example 56

The same experiment as in Example 9 was carried out, except for using tris(methylamino)(diethylamino)silane instead of bis(ethylamino)dicyclopentylsilane. The results are shown in Table 7.

Example 57

The same experiment as in Example 9 was carried out, except for using tris(methylamino)(di-4-methoxyphenylamino)silane instead of bis(ethylamino)dicyclopentylsilane. The results are shown in Table 7.

Example 58

The same experiment as in Example 9 was carried out, except for using tris(methylamino)(dicyclohexylamino)silane instead of bis(ethylamino)dicyclopentylsilane. The polymerization results are shown in Table 7.

Example 59

Bulk polymerization of propylene was carried out under the same conditions, except for using bis(methylamino)bis(t-butylamino)silane instead of bis(ethylamino)dicyclopentylsilane. The polymerization results are shown in Table 7.

Example 60

Bulk polymerization of propylene was carried out under the same conditions as in Example 9, except for using bis(methylamino)bis(perhydroisoquinolino)silane instead of bis(ethylamino)dicyclopentylsilane. The polymerization results are shown in Table 7.

Example 61

Bulk polymerization of propylene was carried out under the same conditions as in Example 9, except for using tris (ethylamino)(perhydroisoquinolino)silane instead of bis(ethylamino)dicyclopentylsilane. The polymerization results are shown in Table 7.

Example 62

The same experiment as in Example 9 was carried out, except for using tris(methylamino)(cyclohexylamino)silane instead of bis(ethylamino)dicyclopentylsilane. The polymerization results are shown in Table 7.

Example 63

The same experiment as in Example 9 was carried out, except for using (methylamino)(ethylamino)diisopropylsilane instead of bis(ethylamino)dicyclopentylsilane. The polymerization results are shown in Table 8.

Example 64

The same experiment as in Example 9 was carried out, except for using (methylamino)(n-propylamino)diisopropylsilane instead of bis(ethylamino)dicyclopentylsilane. The polymerization results are shown in Table 8.

Example 65

The same experiment as in Example 9 was carried out, except for using (methylamino)(ethylamino)dicyclopentylsilane instead of bis(ethylamino)dicyclopentylsilane. The polymerization results are shown in Table 8.

Example 66

The same experiment as in Example 9 was carried out, except for using (methylamino)(n-propylamino)dicyclopentylsilane instead of bis(ethylamino)dicyclopentylsilane. The polymerization results are shown in Table 8.

Example 67

The same experiment as in Example 9 was carried out, except for using (methylamino)(ethylamino)$_t$-butylethylsilane instead of bis(ethylamino)dicyclopentylsilane. The polymerization results are shown in Table 8.

Example 68

The same experiment as in Example 9 was carried out, except for using (methylamino)(n-propylamino)t-butylethylsilane instead of bis(ethylamino)dicyclopentylsilane. The polymerization results are shown in Table 8.

Example 69

The same experiment as in Example 9 was carried out, except for using (methylamino)(ethylamino)di-t-butylsilane instead of bis(ethylamino)dicyclopentylsilane. The polymerization results are shown in Table 8.

Example 70

The same experiment as in Example 9 was carried out, except for using (methylamino)(n-propylamino)di-t-butylsilane instead of bis(ethylamino)dicyclopentylsilane. The polymerization results are shown in Table 8.

Example 71

The same experiment as in Example 9 was carried out, except for using (methylamino)(n-propylamino)(t-butylamino)ethylsilane instead of bis(ethylamino)dicyclopentylsilane. The polymerization results are shown in Table 8.

Example 72

The same experiment as in Example 9 was carried out, except for using (methylamino)(n-propylamino)bis(isoquinolyl)silane instead of bis(ethylamino)dicyclopentylsilane. The polymerization results are shown in Table 8.

Example 73

The same experiment as in Example 9 was carried out, except for using (methylamino)(ethylamino)bis(diethylamino)silane instead of bis(ethylamino)dicyclopentylsilane. The polymerization results are shown in Table 8.

Example 74

The same experiment as in Example 9 was carried out, except for using bis(methylamino)(n-propylamino)(diethylamino)silane instead of bis(ethylamino)dicyclopentylsilane. The polymerization results are shown in Table 8.

Example 75

Synthesis of Aminosilane Compound

A flask in which the internal atmosphere was sufficiently replaced with highly pure nitrogen gas was charged with a THF solution of methylamine. The solution was cooled to −10 to 0° C. and a hexane solution of commercially available butyl lithium, in an amount equimolar to ethylamine, was slowly added using a dripping funnel while stirring. After the addition, the temperature was gradually increased to 50° C. and the mixture was reacted for two hours to obtain a slurry of lithium salt of methylamine. Another flask in which the internal atmosphere was sufficiently replaced with highly pure nitrogen gas was charged with a toluene solution of bis(methoxy)di-t-butylsilane (a commercially available product) which was cooled to −10 to 0° C., and the above slurry of lithium salt of methylamine, in an amount 2.1 times mol of the bis(methoxy)di-t-butylsilane, was slowly added using an injector in a nitrogen stream. After the addition, the temperature was gradually increased and the mixture was reacted at 70° C. for four hours. After the reaction, the reaction mixture was filtered in a nitrogen atmosphere and the solid components were washed with a small amount of toluene, thereby separating a solid from liquid. The solvent was evaporated from the solution and the main product of bis(methylamino)di-t-butylsilane was purified by distillation under reduced pressure. The boiling point of the compound was found to be 68° C./5 mmHg. The yield was 86.5%. This product was confirmed to be bis(methylamino)di-t-butylsilane by $^1$H-NMR, IR, and the elementary analysis. The elementary analysis confirmed that the compound consists of C: 62.33% (62.54%), H: 12.98% (13.12%), and N: 12.02% (12.16%) wherein the percentages of the parentheses are theoretical values.

In addition, the IR spectrum had absorption by N—H stretching vibration typical to a secondary amine in the neighborhood of 3400 cm$^{-1}$. The position attributable to protons obtained from the chart of $^1$H-NMR spectrum and the spectrum intensities are as shown in Table 3. The results of these analyses support that the compound obtained was bis(methylamino)-t-butylsilane. $^1$H-NMR and IR were measured under the same conditions as in Example 1.

TABLE 3

| Type of proton | Number of protons | Peak position (ppm) |
|---|---|---|
| Proton of CH$_3$ on t-butyl group | 18 | 0.9763 to 0.9565 (multiplet) |
| Proton of methyl group of methylamino group | 6 | 2.5813 (singlet) |
| Proton of NH of ethylamino group | 2 | 0.2000 (broad singlet) |

Example 76

A polymerization catalyst was prepared and polymerization was carried out in the same manner as in Example 9, except for using 2,2-di(isobutyl)-1,3-dimethoxypropane instead of di-n-butyl phthalate. The results are shown in Table 4.

Example 77

A polymerization catalyst was prepared and polymerization was carried out in the same manner as in Example 9, except for using diethyl 2,3-n-propylsuccinate instead of di-n-butyl phthalate. The results are shown in Table 4.

TABLE 4

| Example | Component (C) | Polymerization activity g-PP/g-cat | HI wt % | BD g/ml | MI g/10 min | Mw/Mn | m.p. °C. |
|---|---|---|---|---|---|---|---|
| Example 9 | bis(ethylamino)dicyclopentylsilane | 50,200 | 97.5 | 0.44 | 170 | | 162 |
| Example 10 | bis(methylamino)-t-butylethylsilane | 48,600 | 98.2 | 0.44 | 85 | | |
| Example 11 | bis(ethylamino)diisopropylsilane | 49,800 | 97.5 | 0.44 | 179 | | |
| Example 12 | bis(methylamino)-t-butylmethylsilane | 47,800 | 98.1 | 0.44 | 80 | | |
| Example 13 | bis(methylamino)dicyclohexylsilane | 50,100 | 97.5 | 0.44 | 72 | 10 | |
| Example 14 | bis(methylamino)cyclohexylmethylsilane | 46,100 | 97.5 | 0.44 | 89 | | |
| Example 15 | bis(methylamino)bis(decahydronaphthyl)silane | 36,100 | 97.5 | 0.44 | 80 | 13 | |
| Example 16 | bis(ethylamino)cyclohexylcyclopentylsilane | 50,100 | 97.8 | 0.44 | 174 | 10 | |
| Example 17 | bis(ethylamino)dicyclopentylsilane | 30,500 | 97.2 | 0.43 | 160 | | |
| Example 18 | bis(ethylamino)dicyclopentylsilane | 35,200 | 97.4 | 0.45 | 135 | | |
| Example 19 | bis(ethylamino)dicyclopentylsilane | 89,400 | 97 | 0.45 | 145 | | |
| Comparative Example 1 | cyclohexylmethyldimethoxysilane | 57,700 | 97.2 | 0.44 | 17 | 7.3 | |
| Comparative Example 2 | bis(diethylamino)dimethoxysilane | 16,500 | 94.4 | 0.43 | 199 | | |
| Comparative Example 3 | diisopropylaminotriethoxysilane | 30,900 | 97.7 | 0.43 | 40 | | |
| Comparative Example 4 | tris(dimethylamino)methoxysilane | 15,300 | 90.3 | 0.44 | 79 | | |
| Comparative Example 5 | cyclohexylmethyldimethoxysilane | 65,000 | 97.5 | 0.44 | 16 | | |
| Example 31 | bis(methylamino)dicyclopentylsilane | 46,200 | 98 | 0.44 | 96 | 5.2 | 163 |
| Example 32 | bis(n-propylamino)dicyclopentylsilane | 45,600 | 97.2 | 0.44 | 148 | 5.8 | 161 |
| Example 76 | bis(ethylamino)dicyclopentylsilane | 45,000 | 96 | 0.44 | 300 | | |
| Example 77 | bis(ethylamino)dicyclopentylsilane | 33,400 | 96 | 0.42 | 160 | 13 | |

TABLE 5

| Example | Component (C) | Polymerization activity g-PP/g-cat | HI wt % | BD g/ml | MI g/10 min | Mw/Mn |
|---|---|---|---|---|---|---|
| Example 20 | tris(methylamino)-t-butylsilane | 42,000 | 97.8 | 0.44 | 200 | — |
| Example 21 | Bis(methylamino)-di-t-butylsilane | 49,800 | 97.6 | 0.44 | 140 | 11 |
| Example 22 | bis(methylamino)cyclohexylcyclopentylsilane | 50,000 | 97 | 0.44 | 160 | — |
| Example 23 | bis(methylamino)cyclohexylthexylsilane | 49,200 | 97 | 0.44 | 100 | 5 |
| Example 24 | bis(ethylamino)-t-butylisobutylsilane | 47,800 | 97.5 | 0.44 | 135 | — |
| Example 25 | bis(methylamino)-di-4-methoxyphenylsilane | 42,000 | 96.8 | 0.44 | 120 | — |
| Example 26 | bis(methylamino)thexylmethylsilane | 49,100 | 97.7 | 0.44 | 120 | — |
| Example 27 | bis(methylamino)didecahydronaphthylsilane | 42,100 | 96.8 | 0.44 | 89 | 14 |
| Example 28 | Tris(methylamino)cyclohexylsilane | 45,000 | 96.8 | 0.44 | 185 | — |

TABLE 6

| Example | Component (C) | Polymerization activity g-PP/g-cat | HI wt % | BD g/ml | MI g/10 min | Mw/Mn |
|---|---|---|---|---|---|---|
| Example 43 | tetrakis(methylamino)silane | 47,400 | 94.6 | 0.44 | 244 | |
| Example 44 | tetrakis(methylamino)silane | 33,300 | 95.2 | 0.44 | 165 | |
| Example 45 | bis(t-butylamino)bis(diethylamino)silane | 47,000 | 96.3 | 0.44 | 160 | |
| Example 46 | bis(perhydroquinolino)bis(diethylamino)silane | 38,200 | 96.8 | 0.44 | 175 | 18 |
| Example 47 | tris(ethylamino)-di-t-butylaminosilane | 49,900 | 97.2 | 0.44 | 210 | 15.8 |
| Example 48 | bis(di-t-butylamino)bis(methylamino)silane | 50,900 | 96.2 | 0.45 | 100 | 17.8 |
| Example 49 | bis(ethylamino)bis(perhydroisoquinolino)silane | 29,600 | 96.2 | 0.43 | 180 | 20 |
| Example 50 | Tris(ethylamino)(diethylamino)silane | 39,600 | 96.8 | 0.44 | 350 | |

TABLE 6-continued

| Example | Component (C) | Polymerization activity g-PP/g-cat | HI wt % | BD g/ml | MI g/10 min | Mw/Mn |
|---|---|---|---|---|---|---|
| Example 51 | bis(ethylamino)bis(diethylamino)silane | 42,000 | 96.5 | 0.44 | 145 | |
| Example 52 | tris(methylamino)(t-butylethylamino)silane | 30,500 | 96.1 | 0.43 | 250 | 12 |
| Example 53 | tris(methylamino)diisopropylaminosilane | 35,200 | 96.3 | 0.44 | 125 | |
| Example 54 | tetrakis(methylamino)silane | 33,100 | 93.2 | 0.44 | 170 | |
| Example 55 | tetrakis(methylamino)silane | 42,000 | 93 | 0.45 | 131 | |

TABLE 7

| Example | Component (C) | Polymerization activity g-PP/g-cat | HI wt % | BD g/ml | MI g/10 min | Mw/Mn |
|---|---|---|---|---|---|---|
| Example 56 | Tris(methylamino)(diethylamino)silane | 37,500 | 97.1 | 0.44 | 160 | — |
| Example 57 | tris(methylamino)(di-4-methoxyphenylamino)silane | 31,000 | 97 | 0.44 | 130 | — |
| Example 58 | tris(methylamino)(dicyclohexylamino)silane | 36,000 | 97 | 0.44 | 180 | — |
| Example 59 | bis(methylamino)bis(t-butylamino)silane | 42,200 | 97.3 | 0.44 | 180 | — |
| Example 60 | bis(methylamino)bis(perhydroisoquinolino)silane | 32,800 | 97.5 | 0.44 | 75 | 13 |
| Example 61 | tris(ethylamino)(perhydroisoquinolino)silane | 41,000 | 97 | 0.44 | 200 | — |
| Example 62 | tris(methylamino)(cyclohexylamino)silane | 31,100 | 97.2 | 0.44 | 150 | — |

TABLE 8

| Example | Component (C) | Polymerization activity g-PP/g-cat | HI wt % | BD g/ml | MI g/10 min | Mw/Mn |
|---|---|---|---|---|---|---|
| Example 63 | (methylamino)(ethylamino)diisopropylsilane | 46,400 | 97.6 | 0.44 | 180 | 8 |
| Example 64 | (methylamino)(n-propylamino)diisopropylsilane | 43,300 | 97.2 | 0.44 | 185 | 9 |
| Example 65 | (methylamino)(ethylamino)dicyclopentylsilane | 49,000 | 97.1 | 0.44 | 165 | 10.3 |
| Example 66 | (methylamino)(n-propylamino)dicyclopentylsilane | 48,200 | 96.1 | 0.44 | 195 | 10.4 |
| Example 67 | (methylamino)(ethylamino)-t-butylethylsilane | 43,900 | 97.3 | 0.44 | 100 | 8.8 |
| Example 68 | (methylamino)(n-propylamino)-t-butylethylsilane | 40,900 | 96.2 | 0.45 | 150 | 10 |
| Example 69 | (methylamino)(ethylamino)-di-t-butylsilane | 45,600 | 97.2 | 0.43 | 95 | 12.01 |
| Example 70 | (methylamino)(n-propylamino)-di-t-butylsilane | 42,600 | 96 | 0.44 | 105 | 16.8 |
| Example 71 | (methylamino)(n-propylamino)(t-butylamino)ethylsilane | 42,000 | 96.7 | 0.44 | 200 | 9.9 |
| Example 72 | (methylamino)(n-propylamino)bis(isoquinolyl)silane | 30,500 | 96.1 | 0.43 | 95 | 18 |
| Example 73 | (methylamino)(ethylamino)bis(diethylamino)silane | 37,200 | 97.1 | 0.44 | 170 | 8.5 |
| Example 74 | bis(methylamino)(n-propylamino)(diethylamino)silane | 37,100 | 97.2 | 0.44 | 151 | 7.9 |

The molecular weight distribution was measured only for polymers prepared in Examples 13, 15, 16, 21, 23, 27, 31, 32, 46, 47, 48, 49, 52, and 60, and Comparative Example 1. It can be seen from the above results that polymers with high stereoregularity can be obtained in a high yield and excellent hydrogen response can be obtained by using an aminosilane compound in the polymerization. It was also found that some aminosilane compounds can broaden the molecular weight distribution of the resulting polymer.

INDUSTRIAL APPLICABILITY

When used as a catalyst component for polymerization of olefins, the novel aminosilane compound and specific aminosilane compounds of the present invention can highly maintain stereoregularity and yield of the polymers and can exhibit excellent hydrogen response when compared with the general catalysts. Therefore, owing to the capability of reducing the amount of hydrogen used for the polymerization and high catalyst activity, the catalyst is expected not only to produce polyolefins for common use at a low cost, but also to be useful in the manufacture of olefin polymers having high functions.

The invention claimed is:

1. A catalyst for polymerization of olefins formed from (A) a solid catalyst component comprising magnesium, titanium, halogen, and an electron donor compound; (B) an organoaluminum compound represented by the following formula (3):

$$R^6_p AlQ_{3-p} \quad (3)$$

wherein $R^6$ represents an alkyl group having 1 to 4 carbon atoms, Q represents a hydrogen atom or a halogen atom, and p represents a real number satisfying the formula $0 < p \leq 3$; and (C) an aminosilane compound represented by formula (2):

$$R^3_n Si(NR^4R^5)_{4-n} \quad (2)$$

wherein $R^3$ represents a linear or branched alkyl group having 1 to 20 carbon atoms, a cycloalkyl group or a derivative thereof, two or more $R^3$'s which may be present being either the same or different; $R^4$ represents a hydrogen atom, a linear or branched alkyl group having 1 to 20 carbon atoms, a cycloalkyl group or a derivative thereof, a vinyl group, an aryl group, or an aralkyl group, two or more $R^4$'s which may be present being either the same or different; $R^5$ represents a linear or branched alkyl group having 1 to 20 carbon atoms, a cycloalkyl group or a derivative thereof, a vinyl group, an aryl group, or an aralkyl group, two or more $R^5$'s which may be present being either the same or different; $R^4$ and $R^5$ may bond to form a ring; n is an integer from 1 to 3; at least one of the $NR^4R^5$ groups is a secondary amino group; and at least one of the $R^3$ groups is a cycloalkyl group or a derivative thereof.

2. The catalyst for polymerization of olefins according to claim 1, wherein the solid catalyst component (A) is prepared by contacting (a) a magnesium compound, (b) a tetravalent titanium halide compound, and (c) an electron donor compound.

3. A process for producing an olefin polymer comprising polymerizing olefins in the presence of the catalyst for polymerization of olefins according to claim 1.

4. The process for producing olefin polymer according to claim 3, wherein the olefins are propylene.

5. The catalyst for polymerization of olefins according to claim 1, wherein in the formula (2), n is 2: $R^4$ is a hydrogen atom; and $R^5$ is a linear or branched alkyl group having 1 to 3 carbon atoms.

6. The catalyst for polymerization of olefins according to claim 1, wherein the aminosilane compound represented by formula (2) is di(alkylamino)cycloalkylalkylsilane or di(alkylamino)dicycloalkylsilane.

7. The catalyst for polymerization of olefins according to claim 1, wherein the aminosilane compound represented by formula (2) is di(alkylamino)cyclohexylmethylsilane.

* * * * *